US012569603B2

(12) United States Patent
Suffritti et al.

(10) Patent No.: US 12,569,603 B2
(45) Date of Patent: Mar. 10, 2026

(54) METHOD FOR CALIBRATING A PERISTALTIC PUMP IN A MEDICAL APPARATUS AND MEDICAL APPARATUS FOR PERFORMING THIS METHOD

(71) Applicants: Baxter Healthcare SA, Glattpark (CH); Baxter International Inc., Deerfield, IL (US)

(72) Inventors: Mauro Suffritti, Medolla (IT); Mauro Gusella, Castelvetro di Modena (IT)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 411 days.

(21) Appl. No.: 18/256,781

(22) PCT Filed: Dec. 10, 2021

(86) PCT No.: PCT/EP2021/085217
§ 371 (c)(1),
(2) Date: Jun. 9, 2023

(87) PCT Pub. No.: WO2022/123021
PCT Pub. Date: Jun. 16, 2022

(65) Prior Publication Data
US 2024/0042114 A1 Feb. 8, 2024

(30) Foreign Application Priority Data
Dec. 10, 2020 (IT) ........................ 102020000030350

(51) Int. Cl.
*A61M 1/28* (2006.01)
*A61M 1/14* (2006.01)

(52) U.S. Cl.
CPC ............ *A61M 1/282* (2014.02); *A61M 1/152* (2022.05); *A61M 1/154* (2022.05);
(Continued)

(58) Field of Classification Search
CPC .... A61M 1/152; A61M 1/154; A61M 1/1562; A61M 1/1563; A61M 1/159;
(Continued)

(56) References Cited

U.S. PATENT DOCUMENTS

| | | | | |
|---|---|---|---|---|
| 6,691,047 B1 * | 2/2004 | Fredericks | ........... | A61M 60/113 |
| | | | | 702/50 |
| 9,089,639 B2 * | 7/2015 | Breuel | ................ | A61M 1/1643 |

(Continued)

FOREIGN PATENT DOCUMENTS

WO WO 2007/133259 A2 * 11/2007
WO 2012129501 A2 9/2012

*Primary Examiner* — John Kim
(74) *Attorney, Agent, or Firm* — K&L Gates LLP

(57) ABSTRACT

A method for calibrating a peristaltic pump in a medical apparatus comprises: rotating the peristaltic pump of a predetermined rotation to pump a liquid from a fluid source from a first compartment into a second compartment of a manifold assembly, raising a level of the liquid in the second compartment and compressing air in an air buffer volume of the manifold assembly; measuring a pressure of air in the air buffer volume; calculating, from the measured pressure, a variation of liquid volume in the second compartment due to the rotation of the peristaltic pump; calculating, from the variation of liquid volume and the predetermined rotation, a stroke liquid volume of the peristaltic pump.

21 Claims, 25 Drawing Sheets

(52) U.S. Cl.
CPC ........ *A61M 1/1562* (2022.05); *A61M 1/1563* (2022.05); *A61M 1/159* (2022.05); *A61M 1/281* (2014.02); *A61M 1/288* (2014.02); *A61M 2205/121* (2013.01); *A61M 2205/123* (2013.01); *A61M 2205/126* (2013.01); *A61M 2205/128* (2013.01); *A61M 2205/3341* (2013.01); *A61M 2205/70* (2013.01); *A61M 2205/7536* (2013.01); *A61M 2206/22* (2013.01)

(58) Field of Classification Search
CPC ...... A61M 1/281; A61M 1/282; A61M 1/288; A61M 2205/121; A61M 2205/123; A61M 2205/126; A61M 2205/128; A61M 2205/3341; A61M 2205/70; A61M 2205/7536; A61M 2206/22
See application file for complete search history.

(56) References Cited

U.S. PATENT DOCUMENTS

| | | | |
|---|---|---|---|
| 9,962,476 B2 * | 5/2018 | Jansson ............... | A61M 1/3413 |
| 2005/0209563 A1 | 9/2005 | Hopping et al. | |

* cited by examiner

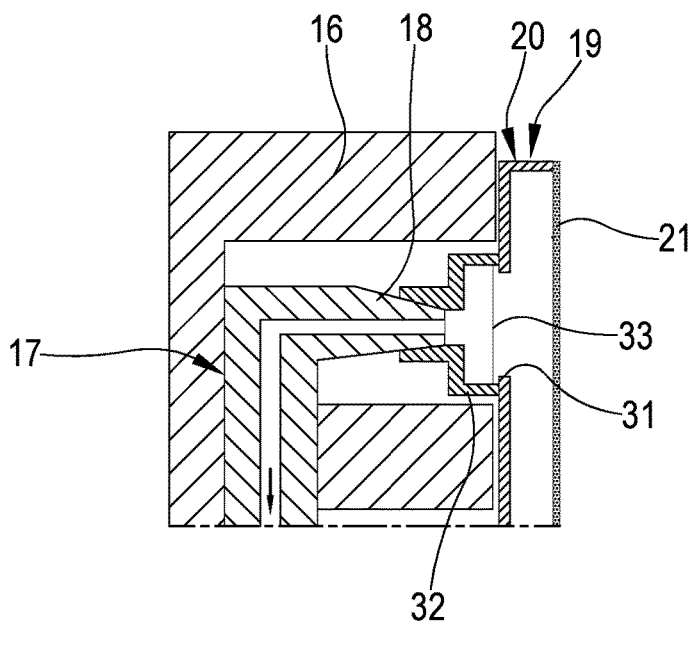
FIG.5
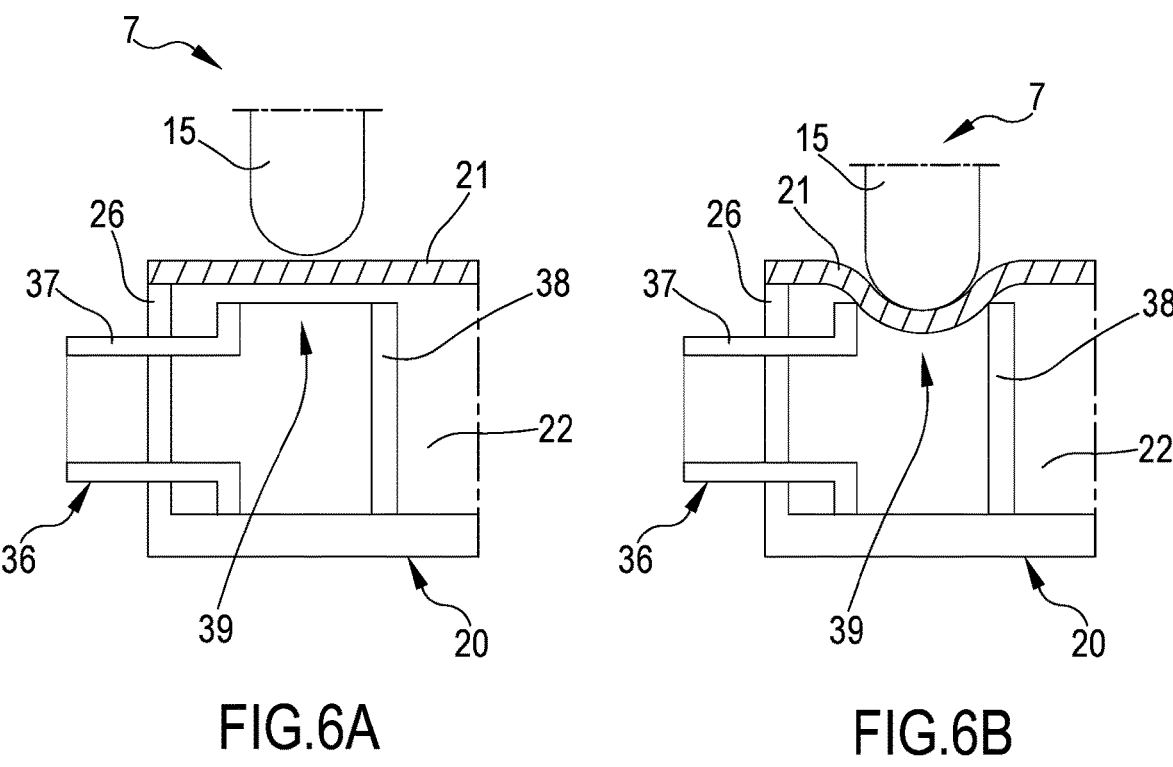
FIG.6A                    FIG.6B

FIG.12

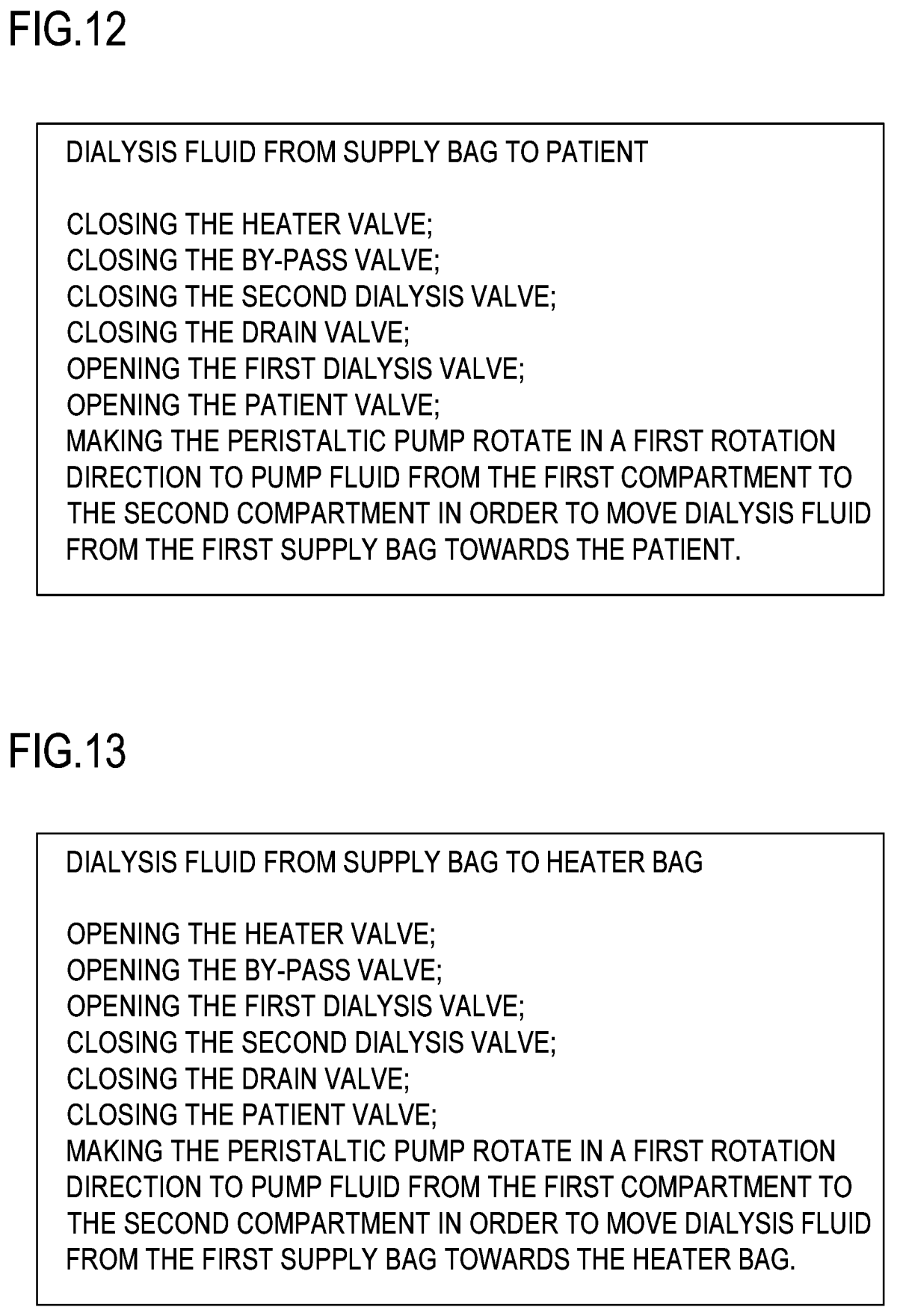

DIALYSIS FLUID FROM SUPPLY BAG TO PATIENT

CLOSING THE HEATER VALVE;
CLOSING THE BY-PASS VALVE;
CLOSING THE SECOND DIALYSIS VALVE;
CLOSING THE DRAIN VALVE;
OPENING THE FIRST DIALYSIS VALVE;
OPENING THE PATIENT VALVE;
MAKING THE PERISTALTIC PUMP ROTATE IN A FIRST ROTATION
DIRECTION TO PUMP FLUID FROM THE FIRST COMPARTMENT TO
THE SECOND COMPARTMENT IN ORDER TO MOVE DIALYSIS FLUID
FROM THE FIRST SUPPLY BAG TOWARDS THE PATIENT.

FIG.13

DIALYSIS FLUID FROM SUPPLY BAG TO HEATER BAG

OPENING THE HEATER VALVE;
OPENING THE BY-PASS VALVE;
OPENING THE FIRST DIALYSIS VALVE;
CLOSING THE SECOND DIALYSIS VALVE;
CLOSING THE DRAIN VALVE;
CLOSING THE PATIENT VALVE;
MAKING THE PERISTALTIC PUMP ROTATE IN A FIRST ROTATION
DIRECTION TO PUMP FLUID FROM THE FIRST COMPARTMENT TO
THE SECOND COMPARTMENT IN ORDER TO MOVE DIALYSIS FLUID
FROM THE FIRST SUPPLY BAG TOWARDS THE HEATER BAG.

FIG.14

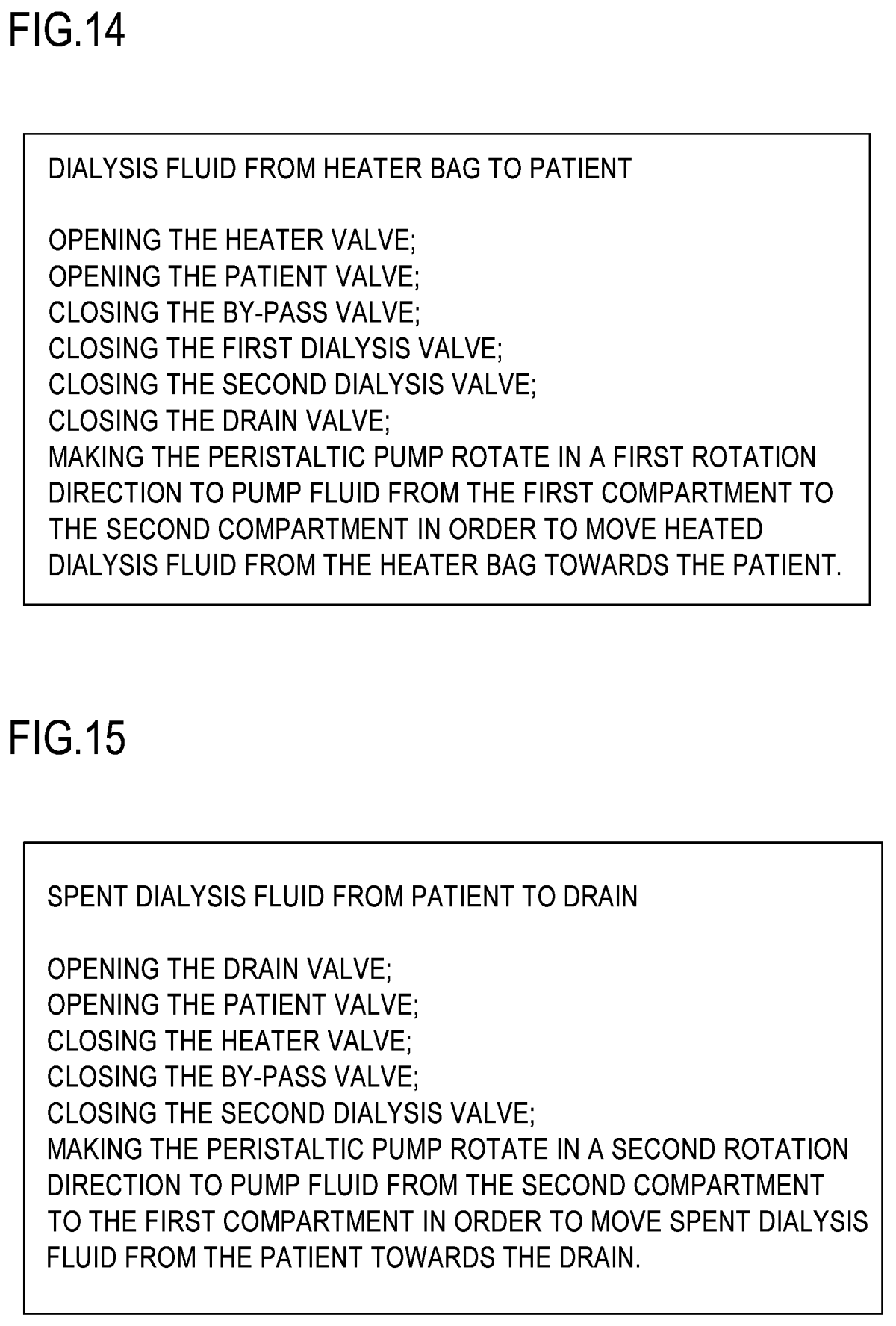

DIALYSIS FLUID FROM HEATER BAG TO PATIENT

OPENING THE HEATER VALVE;
OPENING THE PATIENT VALVE;
CLOSING THE BY-PASS VALVE;
CLOSING THE FIRST DIALYSIS VALVE;
CLOSING THE SECOND DIALYSIS VALVE;
CLOSING THE DRAIN VALVE;
MAKING THE PERISTALTIC PUMP ROTATE IN A FIRST ROTATION
DIRECTION TO PUMP FLUID FROM THE FIRST COMPARTMENT TO
THE SECOND COMPARTMENT IN ORDER TO MOVE HEATED
DIALYSIS FLUID FROM THE HEATER BAG TOWARDS THE PATIENT.

FIG.15

SPENT DIALYSIS FLUID FROM PATIENT TO DRAIN

OPENING THE DRAIN VALVE;
OPENING THE PATIENT VALVE;
CLOSING THE HEATER VALVE;
CLOSING THE BY-PASS VALVE;
CLOSING THE SECOND DIALYSIS VALVE;
MAKING THE PERISTALTIC PUMP ROTATE IN A SECOND ROTATION
DIRECTION TO PUMP FLUID FROM THE SECOND COMPARTMENT
TO THE FIRST COMPARTMENT IN ORDER TO MOVE SPENT DIALYSIS
FLUID FROM THE PATIENT TOWARDS THE DRAIN.

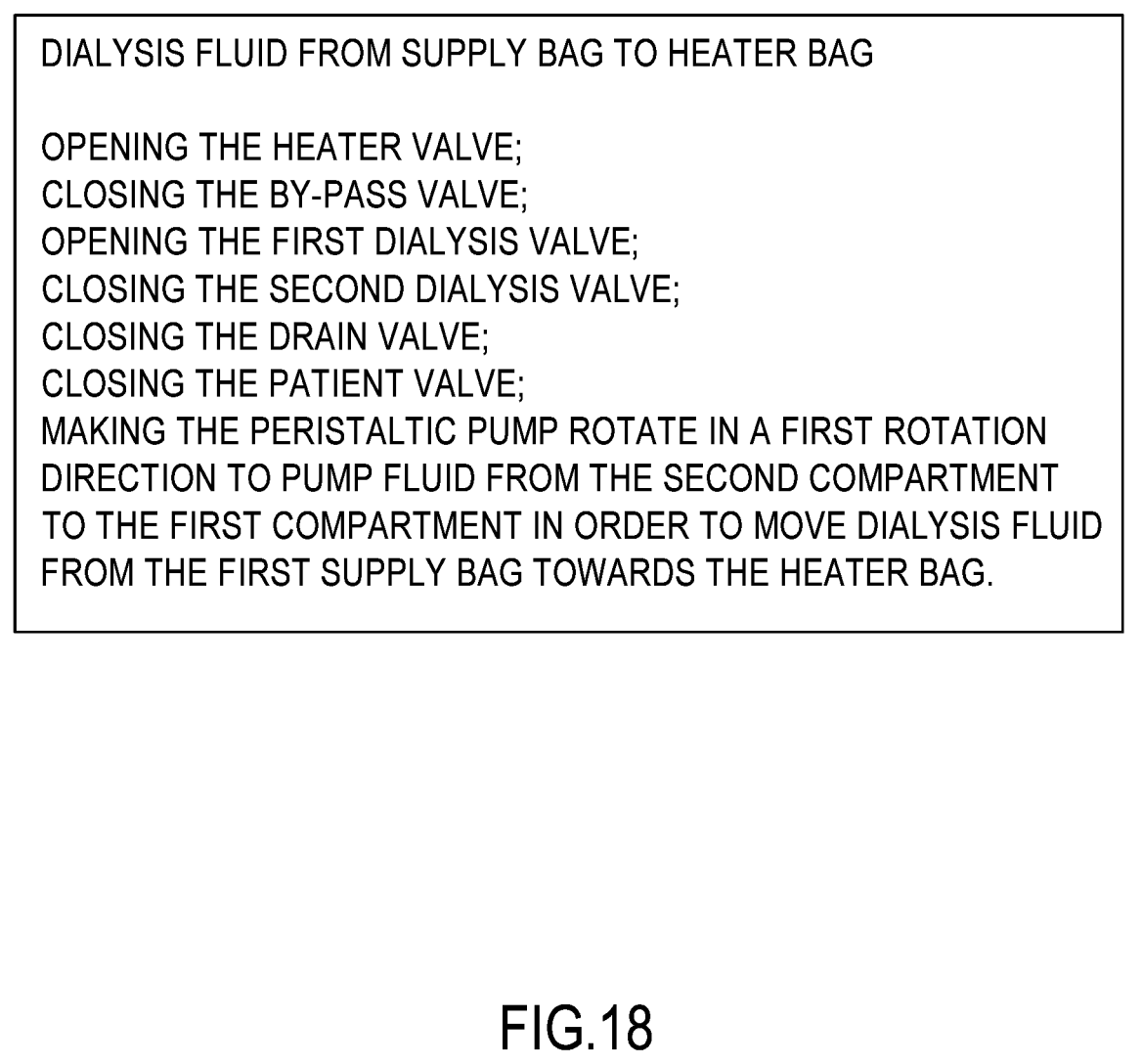

DIALYSIS FLUID FROM SUPPLY BAG TO HEATER BAG

OPENING THE HEATER VALVE;
CLOSING THE BY-PASS VALVE;
OPENING THE FIRST DIALYSIS VALVE;
CLOSING THE SECOND DIALYSIS VALVE;
CLOSING THE DRAIN VALVE;
CLOSING THE PATIENT VALVE;
MAKING THE PERISTALTIC PUMP ROTATE IN A FIRST ROTATION
DIRECTION TO PUMP FLUID FROM THE SECOND COMPARTMENT
TO THE FIRST COMPARTMENT IN ORDER TO MOVE DIALYSIS FLUID
FROM THE FIRST SUPPLY BAG TOWARDS THE HEATER BAG.

FIG.18

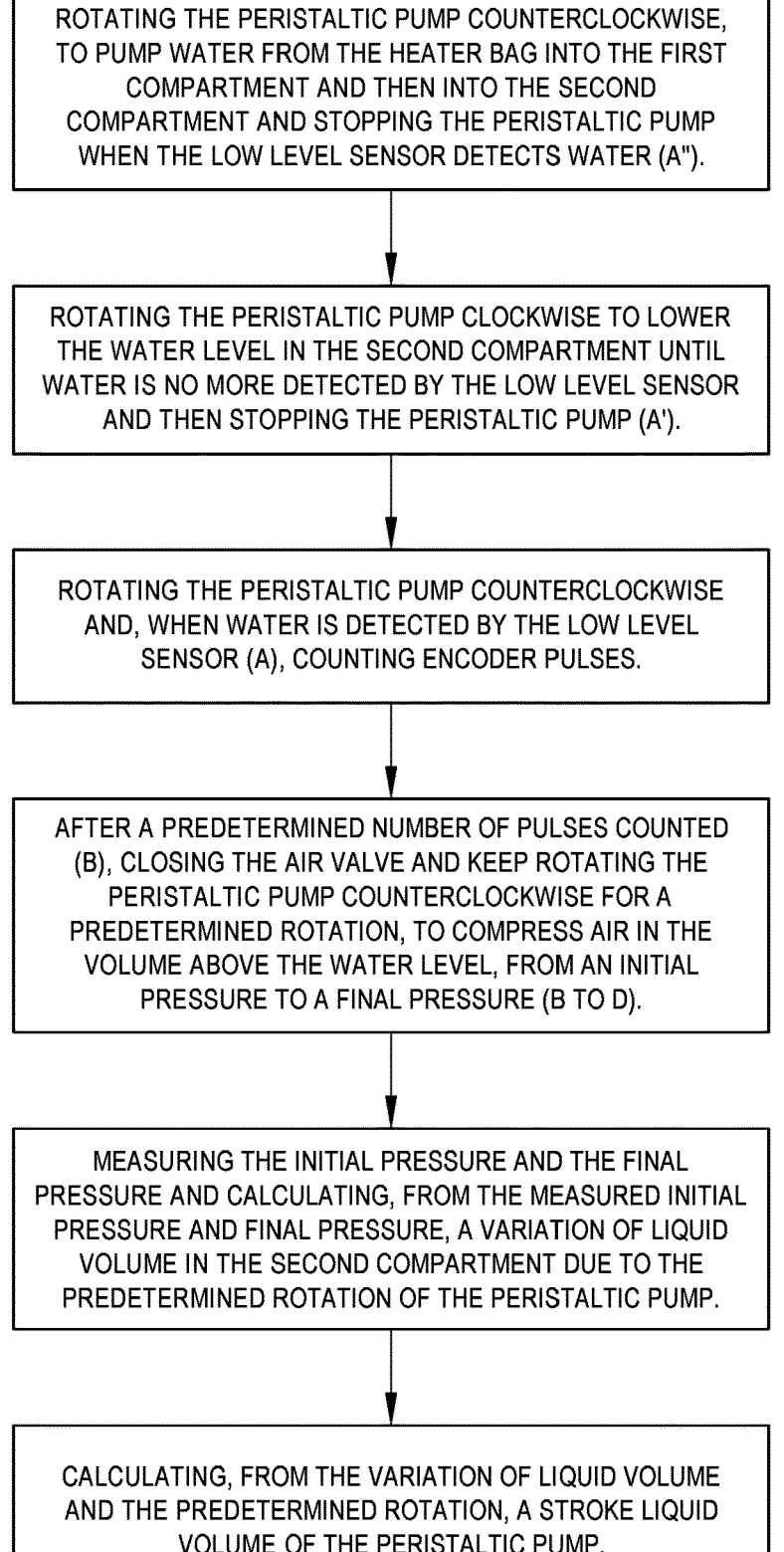

ROTATING THE PERISTALTIC PUMP COUNTERCLOCKWISE, TO PUMP WATER FROM THE HEATER BAG INTO THE FIRST COMPARTMENT AND THEN INTO THE SECOND COMPARTMENT AND STOPPING THE PERISTALTIC PUMP WHEN THE LOW LEVEL SENSOR DETECTS WATER (A").

ROTATING THE PERISTALTIC PUMP CLOCKWISE TO LOWER THE WATER LEVEL IN THE SECOND COMPARTMENT UNTIL WATER IS NO MORE DETECTED BY THE LOW LEVEL SENSOR AND THEN STOPPING THE PERISTALTIC PUMP (A').

ROTATING THE PERISTALTIC PUMP COUNTERCLOCKWISE AND, WHEN WATER IS DETECTED BY THE LOW LEVEL SENSOR (A), COUNTING ENCODER PULSES.

AFTER A PREDETERMINED NUMBER OF PULSES COUNTED (B), CLOSING THE AIR VALVE AND KEEP ROTATING THE PERISTALTIC PUMP COUNTERCLOCKWISE FOR A PREDETERMINED ROTATION, TO COMPRESS AIR IN THE VOLUME ABOVE THE WATER LEVEL, FROM AN INITIAL PRESSURE TO A FINAL PRESSURE (B TO D).

MEASURING THE INITIAL PRESSURE AND THE FINAL PRESSURE AND CALCULATING, FROM THE MEASURED INITIAL PRESSURE AND FINAL PRESSURE, A VARIATION OF LIQUID VOLUME IN THE SECOND COMPARTMENT DUE TO THE PREDETERMINED ROTATION OF THE PERISTALTIC PUMP.

CALCULATING, FROM THE VARIATION OF LIQUID VOLUME AND THE PREDETERMINED ROTATION, A STROKE LIQUID VOLUME OF THE PERISTALTIC PUMP.

FIG.29

METHOD FOR CALIBRATING A PERISTALTIC PUMP IN A MEDICAL APPARATUS AND MEDICAL APPARATUS FOR PERFORMING THIS METHOD

PRIORITY CLAIM

This application is a national phase entry of PCT/EP2021/085217, filed Dec. 10, 2021, which claims priority to Italian Patent Application No. 102020000030350, filed Dec. 10, 2020, the entire disclosures of which are incorporated herein by reference.

TECHNICAL FIELD

The present disclosure relates to a medical apparatus of the type comprising a medical machine and a manifold assembly configured to transfer a fluid to be exchanged with or transferred to or recovered from a patient through a peristaltic pump. For instance, the medical apparatus may be a peritoneal dialysis apparatus or an extracorporeal blood treatment apparatus.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is peritoneal dialysis (PD), which infuses a dialysis solution, also called dialysis fluid, into a patient's peritoneal chamber via a catheter. The dialysis fluid is in contact with the peritoneal membrane in the patient's peritoneal chamber. Waste, toxins and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times.

Extracorporeal blood treatment involves removing blood from a patient, treating the blood externally to the patient, and returning the treated blood to the patient. Extracorporeal blood treatment is typically used to extract undesirable matter or molecules from the patient's blood and add desirable matter or molecules to the blood. Extracorporeal blood treatment is used with patients unable to effectively remove matter from their blood, such as when a patient has suffered temporary or permanent kidney failure. These patients and other patients may undergo extracorporeal blood treatment to add or remove matter to their blood, to maintain an acid/base balance or to remove excess body fluids, or to perform extracorporeal gas exchange processes, for example.

BACKGROUND

Systems of this kind, like a peritoneal dialysis apparatus or an extracorporeal blood treatment apparatus, are configured to manage fluids, like medical fluids and/or blood, and comprise peristaltic pumps to move said fluids.

Use of peristaltic pumps are known in the field of medical apparatuses. A peristaltic pump comprises a pump rotor provided with one or more rollers. A yieldable tube segment is positioned in part around the rotor to be squeeze by the roller or rollers when the rotor is rotated through a motor to move the fluid inside the yieldable tube segment.

A main drawback of this kind of pump assemblies is that peristaltic pumps and fluid pump segments do not have enough accuracy in order to address the volumetric measure requirements of modern medical apparatuses, like apparatuses for peritoneal dialysis (PD) and/or hemodialysis (HD).

A possible solution to obviate this drawback is to increase the quality of the assembly (pumps and tube segments) but this would increase the resulting manufacturing costs and provide off-market selling prices.

Another possible solution is to regularly calibrate the peristaltic pumps, i.e. to estimate the stroke volume used to calculate the flow rate.

Document WO2007133259 discloses a method for calibrating a plurality of pumps in a blood processing apparatus. A first pump is calibrated through a reservoir and a fluid level sensor. After the first pump has been calibrated, the remaining pumps may be calibrated with respect to the first pump.

Document U.S. Pat. No. 9,962,476 discloses a dialysis fluid distribution system comprising first and second volumetric pumps, a calibration chamber and a level detector.

Document U.S. Pat. No. 6,691,047 discloses a method of calibrating a peristaltic pump in medical instruments. The step of calibrating comprises the steps of: moving a known volume of fluid with the pump at a predetermined pump revolutions per minute; measuring the time taken to move the known volume of fluid and determining the volume of fluid moved by the pump per revolution.

Document WO2012129501 discloses an automated peritoneal dialysis system including prescription-driven dialysis fluid preparation, an integrated disposable fluid circuit, and sensor capabilities that allow accurate filing and draining control with high safety margins. To provide enhanced accuracy, one or more pump calibration and/or flow path compensation parameters may be generated through a calibration procedure. fluid is pumped between any or all of the paths identified above. A calibration coefficient is generated for each of the relevant fluid paths and stored in a memory as a parameter representing the number of ml/per pump rotation. The actual fluid quantity transported during the calibration step is measured by a flow meter.

Document US2005209563 discloses a method for calibrating a peristaltic pump in a medical apparatus. A function that models the effects of inputted or measured variables is provided. The variables are measured by pressure sensors, a fluid temperature sensor and a tachometer for the rotational speed of the pump motor. The function also comprises constants that are determined empirically or received via data.

Document U.S. Pat. No. 9,089,639 discloses to calculate a base correction factor for pumps in an extracorporeal blood treatment apparatus. When controlling the pumps to convey fluids, the correction factor is taken into account.

A main identified disadvantage of the known systems refers to the use of additional equipment, with respect to standard equipment of a medical apparatus, to perform calibration.

Other identified disadvantages of the known systems relate to the still low accuracy and considerable complexity of the know calibration systems.

It is therefore an object of the present invention to improve accuracy and reliability of methods used to calibrate peristaltic pumps in medical apparatuses, i.e. to identify the real stroke volume of the tube segments used, in order to accurately measure the flow rates during treatment of patients.

It is a further object of the present invention to provide a simple and fast method for calibrating the peristaltic pumps of medical apparatuses.

It is an object of the present invention to provide a calibration method using devices and/or elements already part of the medical apparatus or changing only in part the existing devices/elements, in order to limit the cost of the equipment employed for calibration.

SUMMARY

At least one of the above objects is substantially reached by a method for calibrating a peristaltic pump of a medical apparatus and by a medical apparatus for performing said method according to one or more of the appended claims.

A method for calibrating a peristaltic pump of a medical apparatus and a medical apparatus for performing said method according to aspects of the invention and capable of achieving one or more of the above objects are here below disclosed.

A $1^{st}$ aspect concerns a method for calibrating a peristaltic pump in a medical apparatus.

A $2^{nd}$ aspect concerns a medical apparatus comprising a medical machine and a manifold assembly, wherein the medical apparatus is configured to perform a method for calibrating a peristaltic pump.

The medical machine comprises: a peristaltic pump having at least one pressing element optionally a plurality of pressing elements, a pressure transducer and a control unit operatively connected at least to the peristaltic pump and to the pressure transducer.

The manifold assembly comprises: a casing delimiting internally a first compartment and a second compartment; a yielding pump tube having a first end connected to the first compartment and a second end connected to the second compartment, wherein the yielding pump tube extends outside the casing and is coupled to the peristaltic pump of the medical machine; a plurality of line tubes each having a first end connected to the first compartment or to the second compartment and a second end connected or connectable to a fluid source or to a drain or to a patient; wherein, when the manifold assembly is properly mounted on the medical machine, an upper part of the second compartment delimits an air buffer volume, the air buffer volume being in communication with the pressure transducer.

The method for calibrating the peristaltic pump comprises: i. rotating the peristaltic pump of a predetermined rotation to pump a liquid from the fluid source into the second compartment and raise a level of the liquid in the second compartment to compress air in the air buffer volume; ii. measuring pressure of air in the air buffer volume; iii. calculating, from the measured pressure of air in the air buffer volume, a variation of liquid volume in the second compartment due to the rotation of the peristaltic pump; iv. calculating, from the variation of liquid volume and the predetermined rotation, a stroke liquid volume of the peristaltic pump.

The control unit is configured and/or programmed to calibrate the peristaltic pump.

The control unit is configured and/or programmed to calibrate the peristaltic pump by performing the following steps: rotating the peristaltic pump of a predetermined rotation to pump a liquid from the fluid source into the second compartment and raise a level of the liquid in the second compartment to compress air in the air buffer volume; measuring pressure of air in the air buffer volume; calculating, from the measured pressure of air in the air buffer volume, a variation of liquid volume in the second compartment due to the rotation of the peristaltic pump; calculating, from the variation of liquid volume and the predetermined rotation, a stroke liquid volume of the peristaltic pump.

In a $3^{rd}$ aspect according to any of the previous aspects, rotating the peristaltic pump a predetermined rotation comprises or the control unit is configured and/or programmed to: rotating the peristaltic pump for a plurality of revolutions or of fractions of revolutions.

In a $4^{th}$ aspect according to aspect 3, the plurality of revolutions or fractions of revolutions comprises "n" half-revolutions, optionally wherein "n" is an integer between five and ten.

In a $5^{th}$ aspect according any of the previous aspects, a rotational speed of the peristaltic pump during the predetermined rotation is between 3 rpm and 8 rpm.

In a $6^{th}$ aspect according to any of aspects 3 to 5, a pressing element of the peristaltic pump or one of a plurality of pressing elements of the peristaltic pump is in a same predetermined position at a start and at an end of the predetermined rotation.

In a $7^{th}$ aspect according to any of the previous aspects, the peristaltic pump comprises an encoder operatively connected to a control unit or to said control unit, wherein the encoder is configured to detect position and movement of the pressing element or elements of the peristaltic pump.

In a $8^{th}$ aspect according to aspect 6 or according to aspect 7 when used with aspect 6, the control unit is configured and/or programmed to detect the predetermined rotation and the predetermined position through the encoder.

In a $9^{th}$ aspect according to any of the previous aspects, the peristaltic pump comprises two pressing elements angularly spaced of 180°.

In a $10^{th}$ aspect according to any of the previous aspects, the yielding pump tube is shaped as a loop comprising a rounded part and two straight parts, wherein the pressing element/s squeeze/s the rounded part during rotation; optionally wherein the loop has an omega "Ω" shape.

In a $11^{th}$ aspect according to any of the previous aspects, the casing comprises a first pump port connected or connectable to the first end of the yielding pump tube and in fluid communication with the first compartment and a second pump port connected or connectable to the second end of the yielding pump tube and in fluid communication with the second compartment, optionally wherein the first pump port and the second pump port diverge from each other away from the casing; optionally the casing further comprises a plurality of ports each connected or connectable to the first end of one line tube.

In a $12^{th}$ aspect according to aspect 10 when used with any of aspects 6 or 8, the predetermined position is at, or close to, a portion between the rounded part and one of the two straight parts.

In a $13^{th}$ aspect according to any of the previous aspects, measuring pressure of air in the air buffer volume comprises:

measuring an initial pressure before air compression and measuring a final pressure after air compression.

In a 14th aspect according to aspect 13, the initial pressure is about 0 mmHg.

In a 15th aspect according to aspect 13 or 14, the final pressure is about 400 mmHg.

In a 16th aspect according to any of the previous aspects, the level of the liquid is raised starting from a first level and, at the end of the predetermined rotation, the liquid is at a second level.

In a 17th aspect according to aspect 16 when according to any of aspects 14 to 16, the variation of liquid volume is calculated as a function of an initial air volume above the first level and of the initial pressure and the final pressure.

In a 18th aspect according to aspect 17 and aspect 4, the stroke liquid volume is a ratio between the variation of liquid volume and a number of half-revolutions of the peristaltic pump contained in the predetermined rotation.

In a 19th aspect according to any of the previous aspects, the medical machine or the manifold comprises at least one level sensor configured to sense a low liquid level in the manifold; optionally the level sensor is a capacitive sensor; optionally the level sensor is placed outside the casing.

In a 20th aspect according to any of aspects 16 to 18 and to aspect 19, the at least one level sensor comprises a low level sensor.

In a 21st aspect according to aspect 20, the first level of liquid is obtained by rotating the peristaltic pump until sensing the low liquid level through the low level sensor and further rotating the peristaltic pump of a predetermined angle to pump an extra volume of liquid above the low liquid level in the second compartment.

In a 22nd aspect according to aspect 21, rotating the peristaltic pump until sensing the low liquid level comprises: rotating the peristaltic pump in a first rotation direction to pump fluid from the first compartment to the second compartment until sensing the low liquid level for a first time and stopping the peristaltic pump.

In a 23rd aspect according to aspect 22, rotating the peristaltic pump until sensing the low liquid level further comprises: rotating the peristaltic pump in a second rotation direction to bring the liquid level below the low liquid level and stopping the peristaltic pump.

In a 24th aspect according to aspect 23, rotating the peristaltic pump until sensing the low liquid level further comprises: rotating again the peristaltic pump in the first rotation direction to reach again the low liquid level and keep on rotating the peristaltic pump to pump the extra volume of liquid.

In a 25th aspect according to any of aspects 21 to 24 and to aspect 6 or 8, the predetermined position of the pressing element is the position at the end of the further rotation of the predetermined angle.

In a 26th aspect according to aspect 25, the control unit is configured and/or programmed to set the predetermined position of the pressing element as the position at the end of the further rotation of the predetermined angle and the peristaltic pump is rotated of said predetermined rotation starting from the predetermined position of the pressing element corresponding to said first level.

In a 27th aspect according to aspect 25 or 26, an air valve is connected to the air buffer volume, wherein the air valve is open before reaching the predetermined position and said air valve is closed once reached to predetermined position and during the following compression.

In a 28th aspect according to aspect 21 or 27, the first level is the level reached at the end of the further rotation of the predetermined angle.

In a 29th aspect according to any of aspects 21 to 28, the predetermined angle is between 80° and 120°.

In a 30th aspect according to any of aspects 20 to 29, a first volume is delimited in the second compartment below the low level sensor.

In a 31st aspect according to aspect 30, said first volume is between 5 ml and 15 ml.

In a 32nd aspect according to any of aspects 21 to 31 and aspect 17 or 18, the initial air volume is a difference between a volume of air above the low liquid level and the extra volume of liquid.

In a 33rd aspect according to any of aspects 20 to 32, the at least one level sensor comprises a high level sensor.

In a 34th aspect according to aspect 33, a high liquid level is sensed through the high level sensor and the rotation of the peristaltic pump is stopped when the pressing element is in the predetermined position for a first time after sensing the high liquid level.

In a 35th aspect according to aspect 33 or 34, a second volume is delimited in the second compartment between the low level sensor and the high level sensor.

In a 36th aspect according to aspect 35, the second volume is between two and four times a nominal stroke liquid volume of the peristaltic pump.

In a 37th aspect according to aspect 36, the second volume is between 15 ml and 25 ml.

In a 38th aspect according to aspect 35 or 36 or 37, a third volume is delimited in the second compartment above the high level sensor.

In a 39th aspect according to aspect 38, the third volume is between 10 ml and 20 ml.

In a 40th aspect according to any of aspects 34 to 39, the method comprises or the control unit is configured and/or programmed to perform the following step: after stopping the rotation of the peristaltic pump and before taking the final pressure, waiting for a stabilizing time and keeping on measuring pressure, to check for possible leakages.

In a 41st aspect according to any of the previous aspects, the casing comprises a breathable membrane configured to put into communication the pressure transducer with the air buffer volume, when the manifold assembly is properly mounted on the medical machine; optionally the breathable membrane is joined to an edge of hole in the casing.

In a 42nd aspect according to aspect 41, the medical machine further comprises an auxiliary chamber in fluid communication with the air buffer volume, optionally through the breathable membrane, and with the pressure transducer; optionally the medical machine comprises an air conduit in air communication with the auxiliary chamber and with the pressure transducer; optionally the air conduit has a coupling end configured to be coupled to the breathable membrane of the casing.

In a 43rd aspect according to aspect 42 and 38 or 39, a fourth volume of the auxiliary chamber is between 20 ml and 30 ml; optionally a sum of the second, third and fourth volume is between 50 ml and 70 ml.

In a 44th aspect according to any of the previous aspects, calculation of the stroke liquid volume through steps i. to iv. is executed consecutively a plurality of times, optionally two to five times, and an average stroke liquid volume is determined.

In a 45th aspect according to any of the previous aspects, the casing has a substantially flattened shape.

In a 46th aspect according to any of the previous aspects, the casing the casing is provided with a front, a back and a plurality of sides; optionally the back is configured to be coupled to a front panel of the medical machine.

In a 47th aspect according to the previous aspect, the first pump port and the second pump port are placed on a first side of the casing while the ports are placed on a second side of the casing, opposite the first side.

In a 48th aspect according to the previous aspect, the casing has a substantially rectangular outline with two long sides and two short sides; optionally, the first side and the second side are both long sides of the casing.

In a 49th aspect according to the previous aspect and to aspect 11, the first pump port and the second pump port are placed on a first side of the casing while the plurality ports are placed on a second side of the casing, opposite the first side.

In a 50th aspect according to the previous aspect, the casing has a substantially rectangular outline with two long sides and two short sides; optionally, the first side and the second side are both long sides of the casing.

In a 51st aspect according to the previous aspect, when the manifold assembly is properly mounted on the medical machine, the two long sides are vertical.

In a 52nd aspect according to any of the previous aspects, the second compartment delimits at least one expansion chamber, optionally a plurality of expansion chambers.

In a 53th aspect according to aspect 52, the casing comprises a recess/protrusion delimiting a respective expansion chamber, such that the expansion chamber has a depth greater than a depth of a remaining part of the second compartment.

In a 54th aspect according to aspect 52 or 53 and to any of aspects 33 to 40, the plurality of expansion chambers comprises: a first expansion chamber, a second expansion chamber and a third expansion chamber; wherein the low level sensor is positioned between the second expansion chamber and the first expansion chamber, wherein the high level sensor is positioned between the third expansion chamber and the second expansion chamber.

In a 55th aspect according to aspect 1 or 2 and according to aspects 4 and 7 and 13 and 16 and 19 and 43, the stroke liquid volume "Stroke_Vol_Press" of the peristaltic pump is calculated through the following formula:

$$
\begin{aligned}
\text{Stroke\_Vol\_Press} = &2*(m/(Zc-Yc))*((V2+V3+V4)- \\
&(\text{Delta\_Encoder\_Pulses}/2m*\text{Stroke\_Vol\_Press}))* \\
&((\text{Pressure\_Final}-\text{Pressure\_Init})/\text{Pressure\_Final}))
\end{aligned}
$$

wherein:

| | |
|---|---|
| m | Number of pulses measured by the encoder per each revolution of the peristaltic pump. |
| Zc – Yc | Number of pulses measured by the encoder during the number of half-revolutions of the peristaltic pump contained in the predetermined rotation. |
| V2 + V3 + V4 | Sum of the second, third and fourth volume. |
| Delta_Encoder_Pulses | Number of pulses measured by the encoder when the liquid level is raised from the low liquid level to the first level. |
| Pressure_Final | Final pressure. |
| Pressure_Init | Initial pressure. |

In a 56th aspect according to any of the previous aspects, the medical machine is a dialysis machine, optionally a cycler for peritoneal dialysis or a machine for extracorporeal treatment of blood.

In a 57th aspect according to any of the previous aspects, the medical apparatus is a dialysis apparatus, optionally a peritoneal dialysis apparatus or an apparatus for extracorporeal treatment of blood.

In a 58th aspect according to any of the previous aspects, the manifold assembly is, at least in part, disposable or reusable.

BRIEF DESCRIPTION OF THE FIGURES

FIG. 5 is a schematic sectional view of a portion of the side view of FIG. 4;

FIGS. 6A and 6B are schematic sectional views of another portion of the assembly taken along section line VI-VI of FIG. 3;

FIGS. 12 to 15 are flow diagrams illustrating the configurations of FIGS. 8 to 11;

FIG. 18 is a flow diagram illustrating the configuration of FIG. 17;

FIG. 29 is a flowchart showing the method of calibration.

DETAILED DESCRIPTION

Embodiment 1

Figure 1:
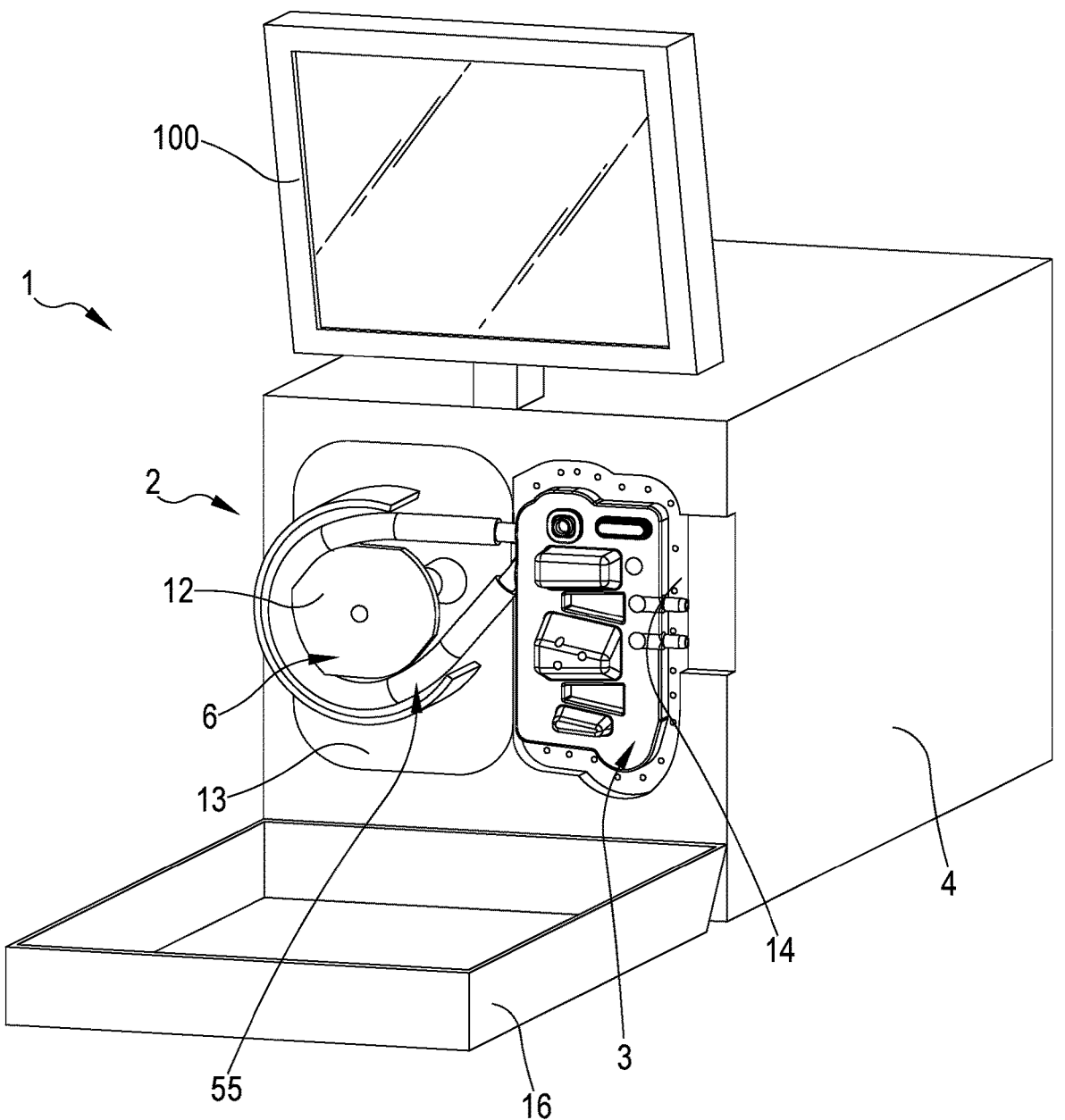
FIG. 1 is a perspective view of one embodiment for an automated peritoneal dialysis apparatus ("APD") of the present disclosure.

Referring now to the FIGS. 1 to 15, an embodiment of a peritoneal dialysis apparatus 1 (APD) comprises a cycler 2 and a manifold assembly 3 (FIGS. 2 and 3) that organizes tubing and performs many functions discussed herein.

The cycler 2 comprises a box 4 housing all the mechanical and electronical parts of the cycler 2. The cycler 2 comprises an electronic control unit 5 (FIG. 4), a roller peristaltic pump 6 (FIG. 1), a plurality of occlusion elements 7, a first or high level sensor 8 and a second or low level sensor 9, a pressure transducer 10 and an air pump 11 (schematically illustrated in FIG. 4). The cycler 2 may also comprise a heater, not shown.

Figure 3:
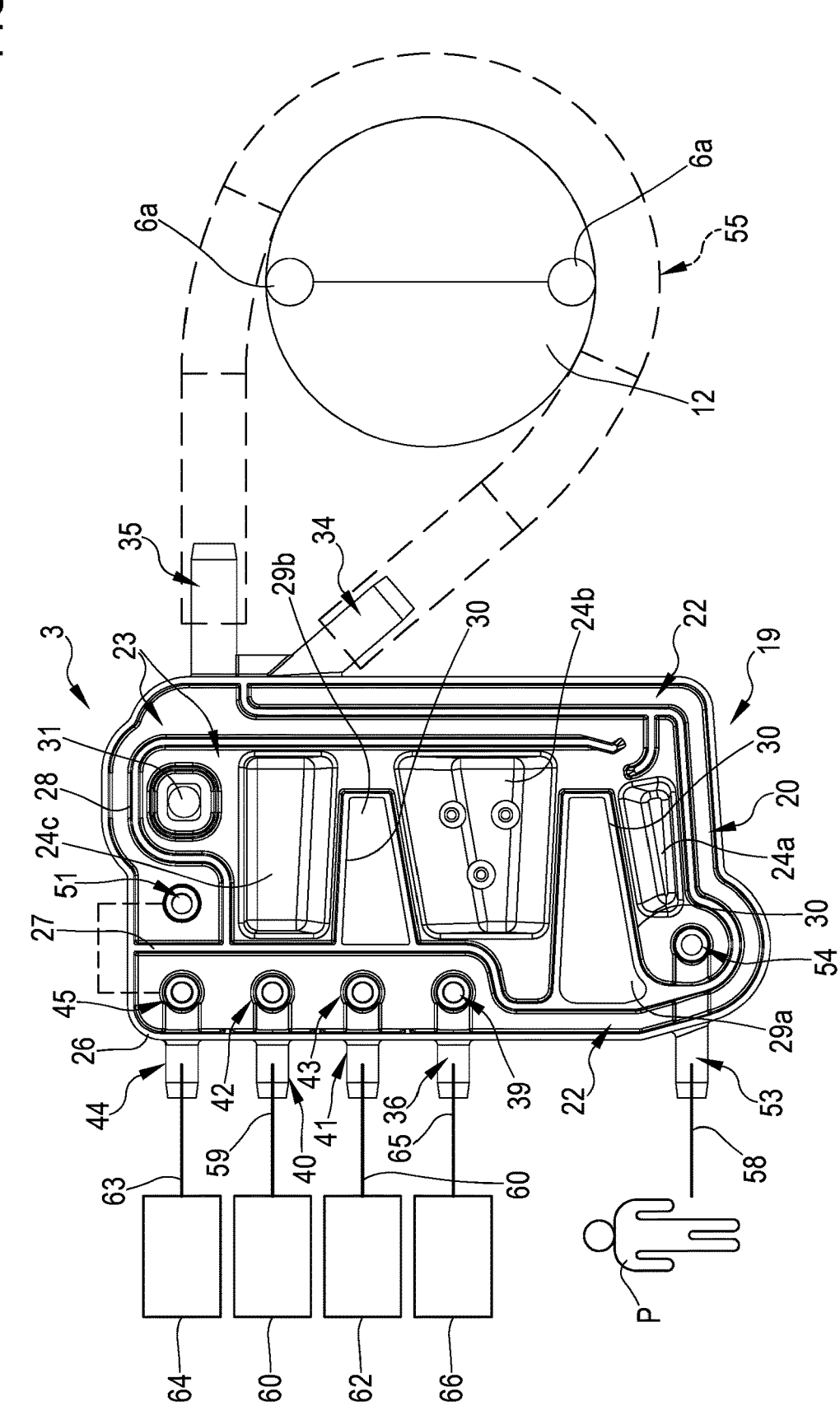
FIG. 3 is a rear view of the manifold assembly of FIG. 2 with some parts removed to illustrate the interior and some other parts schematically represented.
Figure 25:
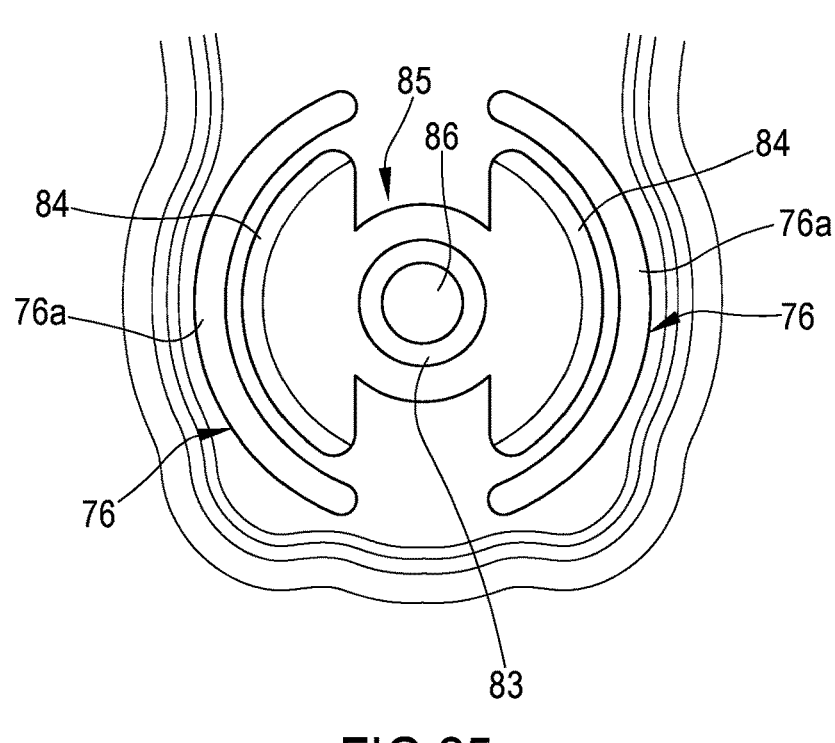
FIG. 25 is a schematic top view of the valve of FIG. 20A and the member of FIG. 24.

The peristaltic pump shown in FIGS. 3 and 25 comprises two pressing rollers 6a angularly spaced of 180°.

A motor, not shown, of the peristaltic pump 6 is housed in the box 4 and a rotor 12 of the peristaltic pump 6 is positioned on a front panel 13 of the box 4 (FIG. 1).

A site 14 of the front panel 13 next to the rotor 6 is configured to retain in removable manner the manifold assembly 3 on said front panel 13. The site 14 may comprise retaining elements configured to be coupled to the manifold assembly 3 and/or the manifold assembly 3 comprises hooking elements configured to hook, in removable manner, said disposable assembly 3 to the front panel 13 of the cycler 2.

The occlusion elements 7 (FIG. 4) protrude from the front panel at the site 14. Each occlusion element 7 comprises a plunger 15 (FIGS. 6A and 6B) moved by a respective actuator, not shown, housed in the box 4. The actuator is configured to move the plunger 15 between a retracted position (FIG. 6A) and a forward position (FIG. 6B), as will be discussed herein.

The cycler 2 comprises a lid 16 (FIGS. 1 and 4) movable between a closed position, in which the lid 16 covers the front panel 13, and an open position, in which the lid 16 is spaced from the front panel 13 to allow a user to access to said front panel 13. The lid 16 of the embodiment of the attached Figures is hinged to the box 4 and may be rotated between the open and the closed position. For sake of simplicity, elements detailed below and belonging to the lid 16 have not been depicted in FIG. 1.

When the manifold assembly 3 is properly mounted on the site 14 of the cycler 2 and the lid 16 is in the closed position, said manifold assembly 3 is closed between the front panel 13 and the lid 16.

Figure 4:
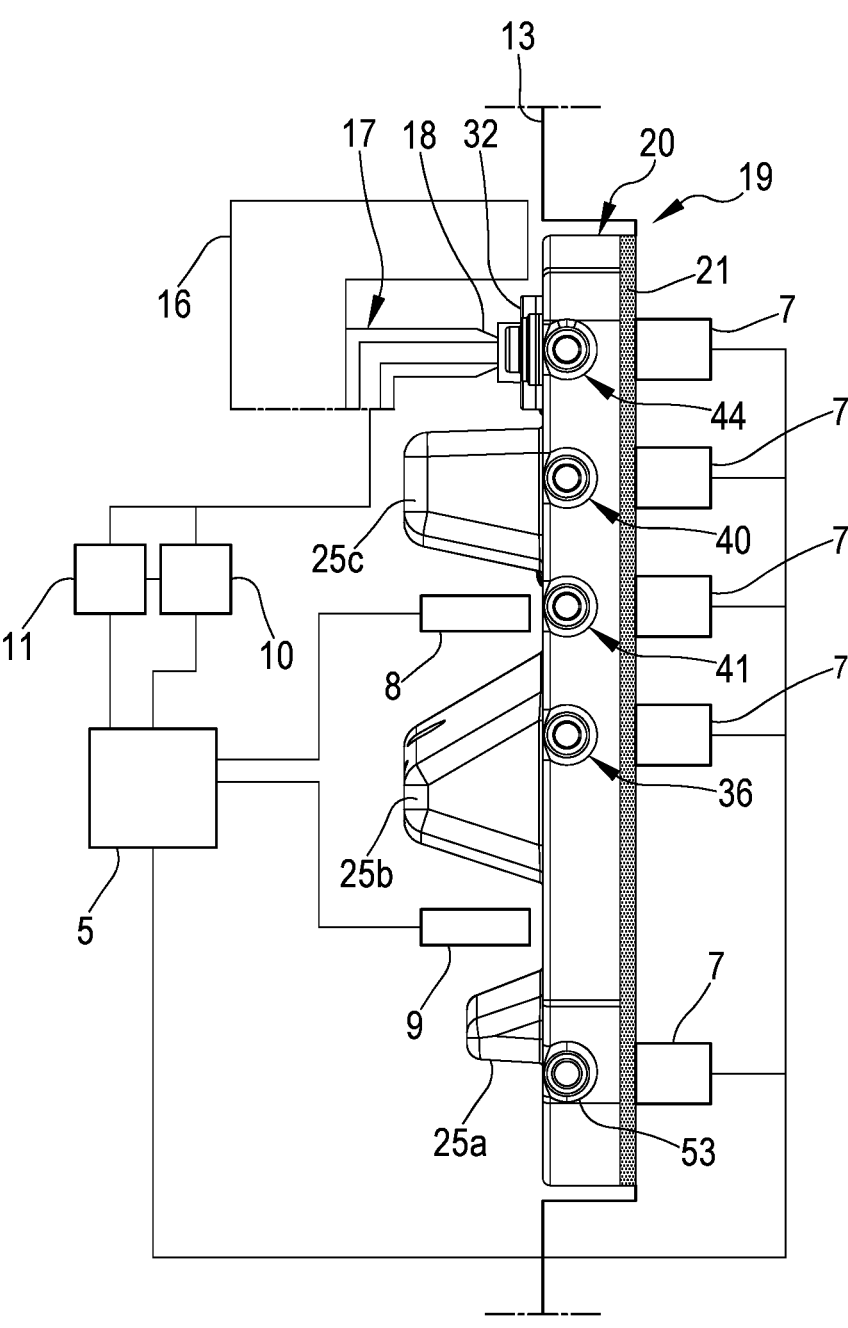
FIG. 4 is a side view of the manifold assembly of FIG. 2.

The first level sensor 8 and the second level sensor 9 are installed on the lid 16 and protrude from a side of the lid 16 configured to face the front panel 13 and/or the manifold assembly 3 when the lid 16 is in the closed position (FIG. 4). The illustrated level sensors 8, 9 are capacitive sensors. In other embodiments, not shown in the attached Figures, the level sensors 8, 9 may be ultrasonic sensors or other type of sensors and/or may be installed on the front panel of the box 4.

An air conduit 17 is mounted on the lid 16 and comprises a coupling end 18. The coupling end 18 is configured to face the manifold assembly 3 when the lid 16 is in the closed position (FIGS. 4 and 5), as will be discussed herein. The air conduit 17 is in air communication with the pressure transducer 10 and the air pump 11. The pressure transducer 10 and the air pump 11 may be installed in the lid 16 or in the box 4.

The control unit 5, schematically shown in FIG. 4, is operationally connected to the motor of the peristaltic pump 6, to the actuators of the occlusion elements 7, to the pressure transducer 10 and the air pump 11, to the first level sensor 8 and second level sensor 9, to the heater and to any other device or sensor of the cycler 2 and is configured/ programmed to control operation of the peritoneal dialysis apparatus 1.

The control unit may be also connected to a display, a keyboard or a touch screen 100 configured to show working parameters of the apparatus 1 and/or to allow a user to set up the apparatus 1 (FIG. 1).

The lid 16 and/or the front panel 13 of the box 4 may also comprise further elements, not shown, configured to manage and route tubing of the manifold assembly 3.

The manifold assembly 3 for the peritoneal dialysis apparatus 1 comprises a disposable casing 19 comprising a rigid molded plastic rigid shell 20, e.g. made of PETG (polyethylene terephthalate glycol-modified) polymer (FIGS. 2, 3 and 4), and a plastic sheet 21, e.g. a polyvinyl chloride soft sheet (FIG. 4). The rigid molded plastic rigid shell 20 delimits a front and sides of the casing 19 and the plastic sheet 21 is a back of the casing 19 (FIG. 4).

Figure 2:
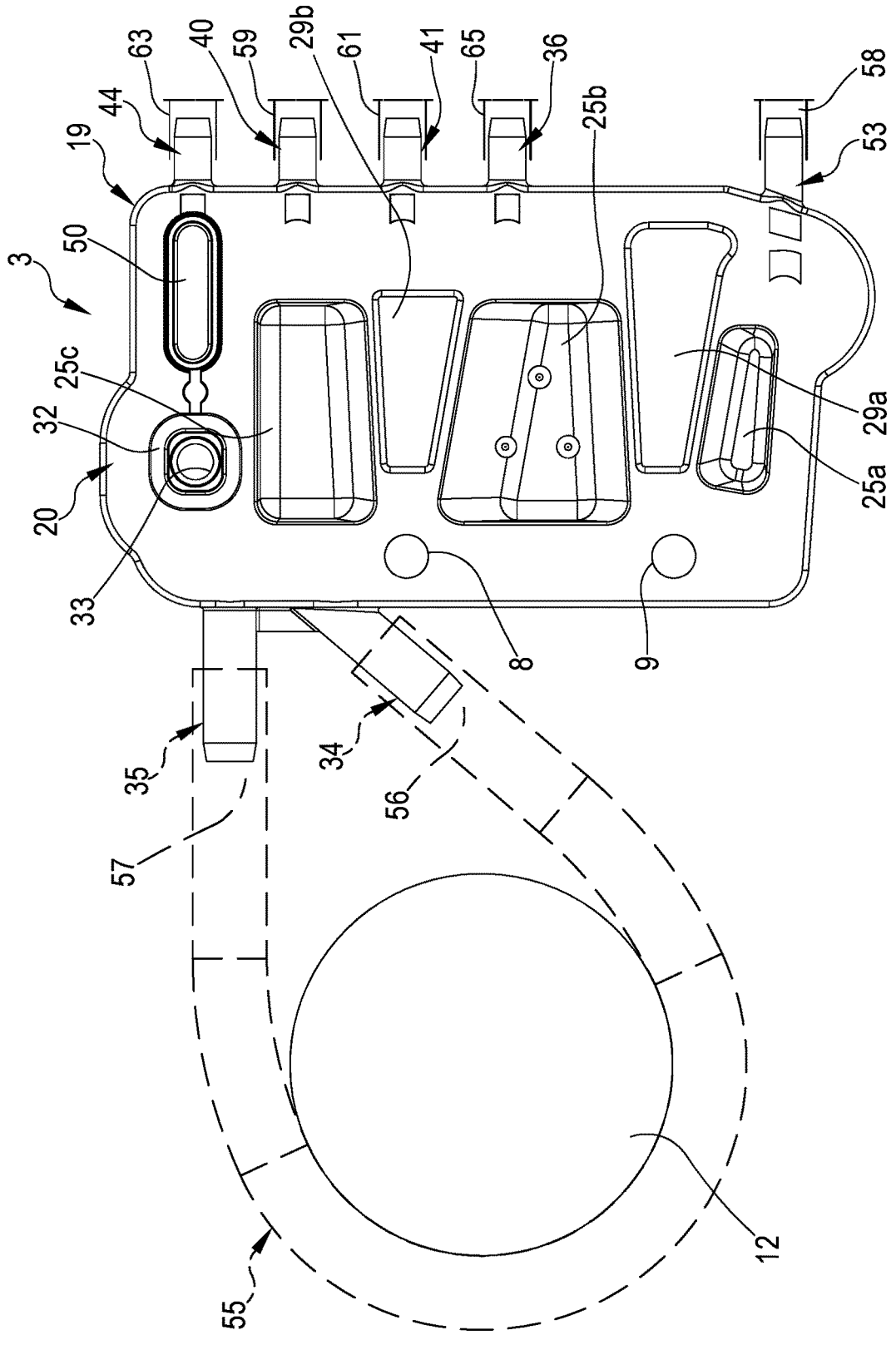
FIG. 2 is a front view of one embodiment for a manifold assembly of the APD apparatus of the present disclosure.

The plastic rigid shell 20 has a substantially flattened shape and comprises septa and recesses on the inner side of the casing 19. Said septa delimit internally a first compartment 22 and a second compartment 23 for fresh and spent dialysis fluid (FIG. 3). Said recesses delimit internally respective three expansion chambers 24a, 24b, 24c and externally, on the front of the casing 19, respective three protrusions 25a, 25b, 25c (FIGS. 2 and 3).

In a front view or back view, the plastic rigid shell 20 and the casing 19 have a substantially rectangular outline with two long sides and two short sides. When the casing 19 is properly mounted on the cycler 2, the two long sides are vertical.

The first compartment 22 is delimited by an outer septum 26 positioned on a peripheral border of the plastic rigid shell 20 and by a first inner septum 27. Referring to the back view of FIGS. 3, 8, 9, 10, 11, the first inner septum 27 has a first extremity connected to the outer septum 26 on the top short side of the plastic rigid shell 20 and a second extremity connected to the outer septum 26 on the right long side of the of the plastic rigid shell 20.

The first inner septum 27 has a substantially U-shape and develops substantially parallel to the left long side, to the bottom short side and to the right long side of the plastic rigid shell 20. The first compartment 22 is a U-shaped first elongated passage.

The second compartment 23 is delimited by the first inner septum 27 and by a portion of the outer septum 26 not delimiting the first compartment 22, such that the second compartment 23 is partly surrounded by the U-shaped first compartment 22.

A second inner septum 28 is positioned inside the second compartment 23 to create a route in the second compartment 23. The second inner septum 28 has a first extremity connected to the first inner septum 27 at a location close to the first extremity of said first inner septum 27 and a second free extremity positioned close to a lower right corner of the plastic rigid shell 20.

Referring to the back view of FIGS. 3, 8, 9, 10, 11, the second inner septum 28 has a substantially inverted L-shape and develops substantially parallel to the top short side and to the right long side of the plastic rigid shell 20. Therefore, the second compartment 23 comprises an inverted L-shaped second elongated passage.

A long stretch of the inverted L-shaped second elongated passage is parallel to a right long stretch of the U-shaped first elongated passage. The second compartment 23 comprises a main central part divided, in part, from the second elongated passage by the second inner septum 28. The second elongated passage has a second extremity communicating with the main central part.

The three expansion chambers 24*a*, 24*b*, 24*c* are fashioned in the main central part of the second compartment 23 and each expansion chamber 24*a*, 24*b*, 24*c* has a depth greater than a depth of a remaining part of the second compartment 23.

Two through apertures 29*a*, 29*b* (FIGS. 2 and 3) pass through the plastic rigid shell 20 and the main central portion of the second compartment 23. These two through apertures are surrounded and delimited by respective further septa 30 connected to the first inner septum 27 Therefore, also these further septa 30 delimit the second compartment 23.

A first aperture 29*a* and a second aperture 29*b* are positioned between two of said three of expansion chambers 24*a*, 24*b*, 24*c*. A first expansion chamber 24*a* of the three expansion chambers 24*a*, 24*b*, 24*c* is close to the bottom short side of the casing 19 and to a short stretch of the U-shaped first elongated passage; a second expansion chamber 24*b* of the three expansion chambers 24*a*, 24*b*, 24*c* is placed between the first aperture 29*a* and the second aperture 29*b*; a third expansion chamber 24*c* of the three expansion chambers 24*a*, 24*b*, 24*c* is placed above the second aperture 29*b*.

An inner volume delimited in the second compartment 23 is greater than an inner volume delimited in the first compartment 22. For instance, the inner volume of the second compartment 23 is about 55 m$^3$ and the inner volume of the first compartment 22 is about 14 m$^3$.

A hole 31 (FIG. 3) is fashioned in the front of the plastic rigid shell 20 located between the third expansion chamber 24*c* and the second inner septum 28. A rigid plastic frame 32 supporting a breathable membrane 33 (FIG. 2) is joined, by welding or gluing, to an edge of the hole 31. The breathable membrane 33 may be of PTFE (polytetrafluoroethylene).

When the assembly 3 is properly mounted on the cycler 2, an upper part of the second compartment 23 provided with the breathable membrane 33 delimits an air buffer volume, as will be discussed herein.

The plastic sheet 21 (FIG. 4) is welded or glued to the plastic rigid shell 20 The plastic sheet 21 is joined to the outer septum 26, the first inner septum 27, the second inner septum 28 and to the further septa 30, to seal the first compartment 22 and the second compartment 23.

The plastic rigid shell 20 comprises a first pump port 34 comprising a hollow cylinder protruding from a right side (in FIGS. 3 and 8-11) of the casing 19. The first pump port 34 is in fluid communication with the first compartment 22. The first pump port 34 opens inside the first compartment 22 at an extremity of the right long stretch of the U-shaped first elongated passage.

The plastic rigid shell 20 comprises a second pump port 35 comprising a hollow cylinder protruding from the right side (in FIGS. 3 and 7-10) of the casing 19. The second pump port 35 is in fluid communication with the second compartment 23. The second pump port 35 opens inside the second compartment 23 at a first extremity of the second elongated passage.

The first pump port 34 and the second pump port 35 are close to each other but separated by the first inner septum 27. The hollow cylinders defining the first pump port 34 and the second pump port 35 diverge from each other away from the casing 19.

The plastic rigid shell 20 comprises a drain port 36 comprising a hollow cylinder 37 protruding from the left side (in FIGS. 3 and 7-10) of the casing 19.

The hollow cylinder 37 of the drain port 36 passes through the outer septum 26 such that said drain port 36 is in fluid communication with the first compartment 22.

The drain port 36 comprises a short hollow barrel 38 connected to the hollow cylinder 37. A central axis of the hollow cylinder 37 is perpendicular to a main axis of the hollow barrel 38 and the cavities delimited inside the hollow cylinder 37 and the hollow barrel 38 are in fluid communication with each other. The hollow barrel 38 protrudes from a bottom surface of the first compartment 22 and opens inside the first compartment 22 (FIGS. 6A and 6B).

The hollow barrel 38 is shorter than the adjacent outer septum 26 (as shown in FIGS. 6A and 6B), than the first inner septum 27, than the second inner septum 28, than the further septa 30, such that the plastic sheet 21 is spaced from an edge of the hollow barrel 38, when said plastic sheet 21 is not deformed, as shown in FIG. 6A.

As will be discussed herein, the edge of the hollow barrel 38 and a part of the plastic sheet 21 facing said edge form a drain valve 39 of the drain port 36.

The plastic rigid shell 20 further comprises a first dialysis port 40 and a second dialysis port 41. Each of these ports 40, 41 protrudes from the left side (in FIGS. 3 and 7-10) of the casing 19 and has the same structure as the drain port 36 detailed above (hollow cylinder 37 and hollow barrel 38).

The first dialysis port 40 and a second dialysis port 41 have a receptive first dialysis valve 42 and a respective second dialysis valve 43.

The plastic rigid shell 20 further comprises a heater port 44 which also protrudes from the left side (in FIGS. 3 and 7-10) of the casing 19 and is structurally similar to the drain port 36 detailed above (hollow cylinder 37 and hollow barrel 38). The heater port 44 has a heater valve 45. The heater port 44 is placed close to an upper left corner of the plastic rigid shell 20.

Figure 7:
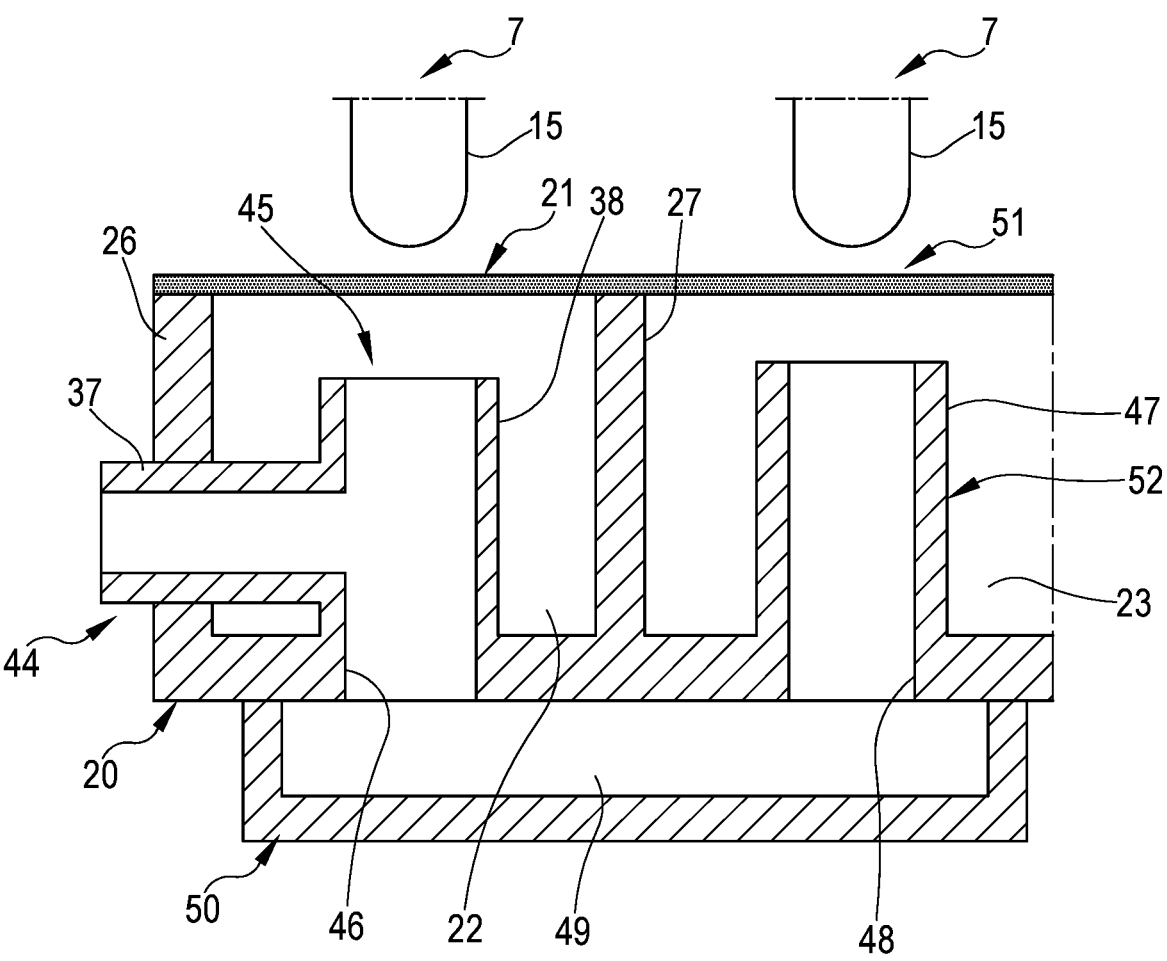
FIG. 7 is a schematic sectional view of another portion of the assembly taken along section line VII-VII of FIG. 3.

Differently from the drain port 36, from the first dialysis port 40 and from the second dialysis port 41, the hollow barrel 38 of the heater port 44 is also in fluid communication with an opening 46 fashioned through the front of the casing 19 (FIG. 7).

The plastic rigid shell 20 comprises a further hollow barrel 47 placed in the second compartment 23 and close to the hollow barrel 38 of the heater port 44. The first inner septum 27 is located between the further hollow barrel 47 and the hollow barrel 38.

The further hollow barrel 47 is in fluid communication with a further opening 48 fashioned through the front of the casing 19 (FIG. 7) and the opening 46 and the further opening 48 are connected by a by-pass channel 49 delimited by a cover 50 welded or glued to the front of the plastic rigid shell 20. The by-pass channel 49 is in fluid communication with the first compartment 22, with the second compartment 23 and with the heater line tube 63.

An edge of the further hollow barrel 47 and a part of the plastic sheet 21 facing said edge form a by-pass valve 51. The further hollow barrel 47 is part of a by-pass port 52 provided with the by-pass valve 51.

Figure 8:
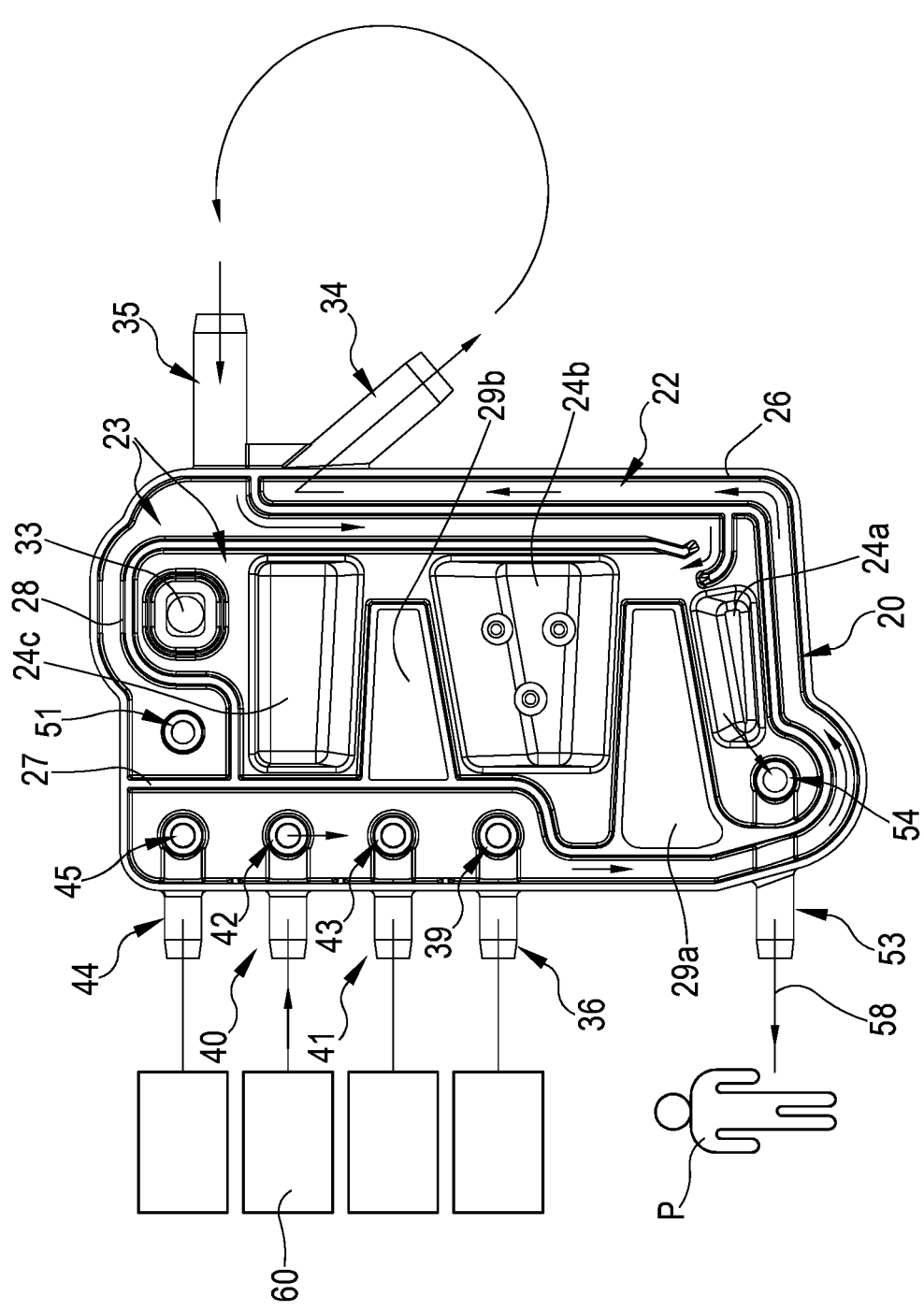
FIGS. 8 to 11 show the rear view of FIG. 3 illustrating respective configurations of the manifold assembly and related liquid flow paths.

The second inner septum 28 separates an area of the second compartment 23 with the hole 31 and the breathable membrane 33 from the by-pass valve 51 (FIGS. 3 and 8).

The plastic rigid shell 20 further comprises a patient port 53. The patient port 53 protrudes from the left side (in FIGS. 3 and 7-10) of the casing 19 and has the same structure as the drain port 36 detailed above (hollow cylinder 37 and hollow barrel 38).

The hollow cylinder 37 of the patient port 53 passes through the outer septum 26 and the first inner septum 27 such that said patient port 53 is in fluid communication with the second compartment 23 (FIG. 3). The patient port 53 has a patient valve 54.

All the valves (drain valve 39, first dialysis valve 42, second dialysis valve 43, heater valve 45, by-pass valve 51, patient valve 54) are structurally and functionally identical and, when the manifold assembly 3 is properly mounted on the cycler 2, they are each placed in front of a respective occlusion element 7 of the cycler 2. Each occlusion element 7 of the cycler 2 is configured to open or close the respective valve (FIGS. 6A and 6B). In other embodiments, not shown in the attached Figures, the occlusion element 7 may be installed on the lid 16 and the structure of the manifold assembly 3 is such to cooperate with said occlusion element 7 on the lid 16.

The hollow cylinders 37 of the heater port 44, the first dialysis port 40, the second dialysis port 41, the drain port 36 and the patient port 53 are parallel with respect to each other. In the embodiment of the attached Figures, when the manifold assembly 3 is properly mounted on the cycler 2, the heater port 44 is above the first dialysis port 40 which in turn is above the second dialysis port 41 which in turn is above the drain port 36 which in turn is above the patient port 53.

The first compartment 22 shaped like a U-shaped first elongated passage extends between the heater port 44 and the first end of the first pump port 34. The second elongated passage has a first extremity connected to the second pump port 35.

The manifold assembly 3 comprises a yielding pump tube 55 having a first end 56 connected to the first pump port 34 and to first compartment 22 and a second end 57 connected to the second pump port 35 and to the second compartment 23 (FIG. 1). The yielding pump tube 55 extends outside the casing 19 and is shaped as a loop or as an eyelet having an omega "Ω" shape to be placed in part around the rotor 12 of the peristaltic pump 6 of the cycler 2.

The manifold assembly 3 further comprises (FIG. 3): a patient line tube 58 having a first end connected to the patient port 53 and a second end connectable to a patient's peritoneal cavity; a first dialysis fluid line tube 59 having a first end connected to the first dialysis port 40 and a second end connected to a first supply bag 60; a second dialysis fluid line tube 61 having a first end connected to the second dialysis port 41 and a second end connected to a second supply bag 62; a heater line tube 63 having a first end connected to the heater port 44 and a second end connected to a heater bag 64; a drain fluid line tube 65 having a first end connected to the drain port 36 and a second end connected to a drain 66.

The patient line tube 58 may extend to a patient line connector, which may for example connect to a patient's transfer set leading to an indwelling catheter that extends to the patient's peritoneal cavity.

The first compartment 22, the yielding pump tube 55 and the second compartment 23 delimit together a fluid path extending between one of the first dialysis fluid line tube 59, second dialysis fluid line tube 61, heater line tube 63, drain fluid line tube 65 and the patient line tube 58, to allow fluid flow from one of the fluid line tubes to the patient line tube 58 or from the patient line tube 58 to one of the fluid line tubes when the peristaltic pump 6 of the cycler 2 is actuated.

The casing 19 of the manifold assembly 3 is mounted on the front panel 13 of the cycler 2, the yielding pump tube 55 is coupled to the rotor 12 and the first dialysis fluid line tube 59, second dialysis fluid line tube 61, heater line tube 63, drain fluid line tube 65 are properly arranged and connected to the respective first supply bag 60, second supply bag 62, heater bag 64 and drain 66. The patient line tube 58 is properly arranged and connected to the patient P. The heater bag 64 is coupled to the heater of the cycler 2.

The shape of the casing 19, with the three protrusions 25*a*, 25*b*, 25*c* and the two through apertures 29*a*, 29*b*, facilitate the user to grab the casing 19 and to mount the casing 19 on the cycler 2.

The user closes the lid 16 so that the first level sensor 8 and the second level sensor 9 are positioned in front of an external flat surface of the casing 19. The position of the first level sensor 8 and the second level sensor 9 when the lid 16 is closed is shown in FIG. 2 and FIG. 4. In FIG. 2 the positions of the first level sensor 8 and second level sensor 9 are schematically represented through dashed line circles.

The first level sensor 8 and the second level sensor 9 are placed one above the other. The first level sensor 8 is positioned between the third expansion chamber 24*c* and the second expansion chamber 24*b*. The second level sensor 9 is positioned between the second expansion chamber 24*b* and the first expansion chamber 24*a*.

When the lid 16 is closed, the coupling end 18 of the air conduit 17 is coupled to the rigid plastic frame 32 supporting the breathable membrane 33 (FIGS. 4 and 5) such that the coupling end 18 faces the breathable membrane 33. This way, the pressure transducer 10 and the air pump 11 of the cycler 2 are put into communication with the breathable membrane 33 and with the upper part of the second compartment 23, i.e. with the air buffer volume.

According to a method for controlling the peritoneal dialysis apparatus 1, the control unit 5 commands the actuators of the occlusion elements 7 to open or close the drain valve 39, first dialysis valve 42, second dialysis valve 43, heater valve 45, by-pass valve 51 and patient valve 54 according to the steps to be performed.

When the valve 54 of the patient port 53 is open, the patient line tube 58 is in fluid communication with the second compartment 23, when the valve 54 of the patient port 53 is closed, fluid communication between the patient line tube 58 and the second compartment 23 is prevented.

When the first dialysis valve 42 of the first dialysis fluid port 40 is open, the first dialysis fluid line tube 59 is in fluid communication with the first compartment 22, when the first dialysis valve 42 of the first dialysis fluid port 40 is closed, fluid communication between the first dialysis fluid line tube 59 and the first compartment 22 is prevented.

When the second dialysis valve 43 of the second dialysis fluid port 41 is open, the second dialysis fluid line tube 61 is in fluid communication with the first compartment 22, when the second dialysis valve 43 of the second dialysis fluid port 41 is closed, fluid communication between the second dialysis fluid line tube 61 and the first compartment 22 is prevented.

When the heater valve 45 of the heater port 44 is open, the heater line tube 63 is in fluid communication with the first compartment 22, when the heater valve 45 of the heater port 44 is closed, fluid communication between the heater line tube 63 and the first compartment 22 is prevented.

When the drain valve 39 of the drain port 36 is open, the drain fluid line tube 65 is in fluid communication with the first compartment 22, when the drain valve 39 of the drain port 36 is closed, fluid communication between the fluid drain line tube 65 and the first compartment 22 is prevented.

When the by-pass valve 51 of the by-pass port 52 is open, the heater line tube 63 is in fluid communication with the second compartment 23; when the by-pass valve 51 of the by-pass port 52 is closed, fluid communication between the heater line tube 63 and the second compartment 23 is prevented.

As shown in FIGS. 6A and 6B and 7, when the actuator keeps the plunger 15 of the occlusion element 7 in the retracted position of FIG. 6A, the plastic sheet 21 is spaced from the edge of the hollow barrel 38 and fluid may flow between the hollow barrel 38 and the first compartment 22 (valve open).

When the actuator moves the plunger 15 of the occlusion element 7 in the forward position of FIG. 6B and keeps plunger 15 in said forward position, the plunger 15 is accommodated in part in the hollow barrel 38.

The plunger 15 pushes, deforms and keeps a portion of plastic sheet 21 against the edge of the hollow barrel 38. The hollow barrel 38 is a seat for the plunger 15 and for the portion of plastic sheet 21 trapped between. A fluid flow between the hollow barrel 38 and the first compartment 22 is prevented (valve closed). All valves work in this way.

Before patient treatment, the manifold assembly 3 is primed. A possible priming sequence is represented in the following table (Table 1).

TABLE 1

| Step | From | To | Valves Open | Pump Direction |
|------|------|-----|-------------|----------------|
| 1 | Heater bag | Drain | By-pass valve Drain valve | ClockWise |
| 2 | First supply bag | Expansion chambers | First dialysis valve | CounterClockWise |
| 3 | Expansion chambers | Drain | Drain valve | Clock Wise |
| 4 | Second supply bag | Expansion chambers | Second dialysis valve | CounterClockWise |
| 5 | Expansion chambers | Drain | Drain valve | ClockWise |
| 6 | Heater bag | Patient | Heater valve Patient valve | CounterClockWise |

Another priming procedure may be performed using communication vessels as disclosed in the following Table 2.

TABLE 2

| Step | From | To | Valves Open | Pump Direction |
|------|------|-----|-------------|----------------|
| 1 | Heater bag | Patient line tube | All valves and yielding pump tube open | — |

After priming, patient treatment may be started.

According to an embodiment of the method for controlling the peritoneal dialysis apparatus 1 (FIGS. 8 and 12), the control unit 5 commands the peritoneal dialysis apparatus 1 to move the dialysis fluid from the first supply bag 60 to the patient P.

The control unit 5 closes and keeps closed the heater valve 45, the by-pass valve 51, the second dialysis valve 43 and the drain valve 39, opens and keeps open the first dialysis valve 42 and the patient valve 54. The control unit 5 commands the motor to rotate the peristaltic pump 6 in a first rotation direction (CounterClockWise in FIG. 8) to pump the dialysis fluid from the first compartment 22 to the second compartment 23.

An auxiliary in-line heater, not shown, may be placed on the first dialysis fluid line tube 59 to heat the dialysis fluid while flowing through said dialysis fluid line tube 59 and towards the patient P.

According to another embodiment of the method for controlling the peritoneal dialysis apparatus 1 (FIGS. 9, 10, 11, 13, 14, 15), the control unit 5 commands the peritoneal dialysis apparatus 1 to move the dialysis fluid from the first supply bag 60 towards the heater bag 64. In this embodiment, the auxiliary in-line heater is not used.

The control unit 5 opens and keeps open the by-pass valve 51 and the first dialysis valve 42 while closes and keeps closed the heater valve 45, the second dialysis valve 43, the drain valve 39 and the patient valve 54. The control unit 5 commands the motor to rotate the peristaltic pump 6 in a first rotation direction (CounterClockWise in FIG. 9) to pump the dialysis fluid from the first compartment 22 to the second compartment 23 and then to the heater bag 64 through the by-pass channel 49.

Once the dialysis fluid has been heated in the heater bag 64 coupled to the heater of the cycler 2, the control unit 5 commands the peritoneal dialysis apparatus 1 to move the heated dialysis fluid from the heater bag 64 towards the patient P.

The control unit 5 opens and keeps open the heater valve 45 and the patient valve 54 and closes and keeps closed the by-pass valve 51, the first dialysis valve 42, the second dialysis valve 43 and the drain valve 39. The control unit 5 commands the motor to rotate the peristaltic pump 6 in a first rotation direction (CounterClockWise in FIG. 10) to pump the dialysis fluid from the first compartment 22 to the second compartment 23.

At the end of the patient treatment, the spent dialysis fluid is removed from the patient P. The control unit 5 commands the peritoneal dialysis apparatus 1 to move the spent dialysis fluid from the patient P towards the drain 66.

The control unit 5 opens and keeps the drain valve 39 and the patient valve 54 and closes and keeps closed the heater valve 45, the by-pass valve 51, the first dialysis valve 42, the second dialysis valve 43. The control unit 5 commands the motor to rotate the peristaltic pump 6 in a second rotation direction (ClockWise in FIG. 11) to pump the dialysis fluid from the second compartment 23 to the first compartment 22.

This treatment sequence is represented in the following table (Table 3).

TABLE 3

| Step | From | To | Valves Open | Pump Direction |
|------|------|-----|-------------|----------------|
| 1 | First supply bag | Heater bag | First dialysis valve By-pass valve | CounterClockWise |
| 2 | Heater bag | Patient | Heater valve Patient valve | CounterClockWise |
| 3 | Patient | Drain | Drain valve Patient valve | ClockWise |

Embodiment 2

Figure 16:
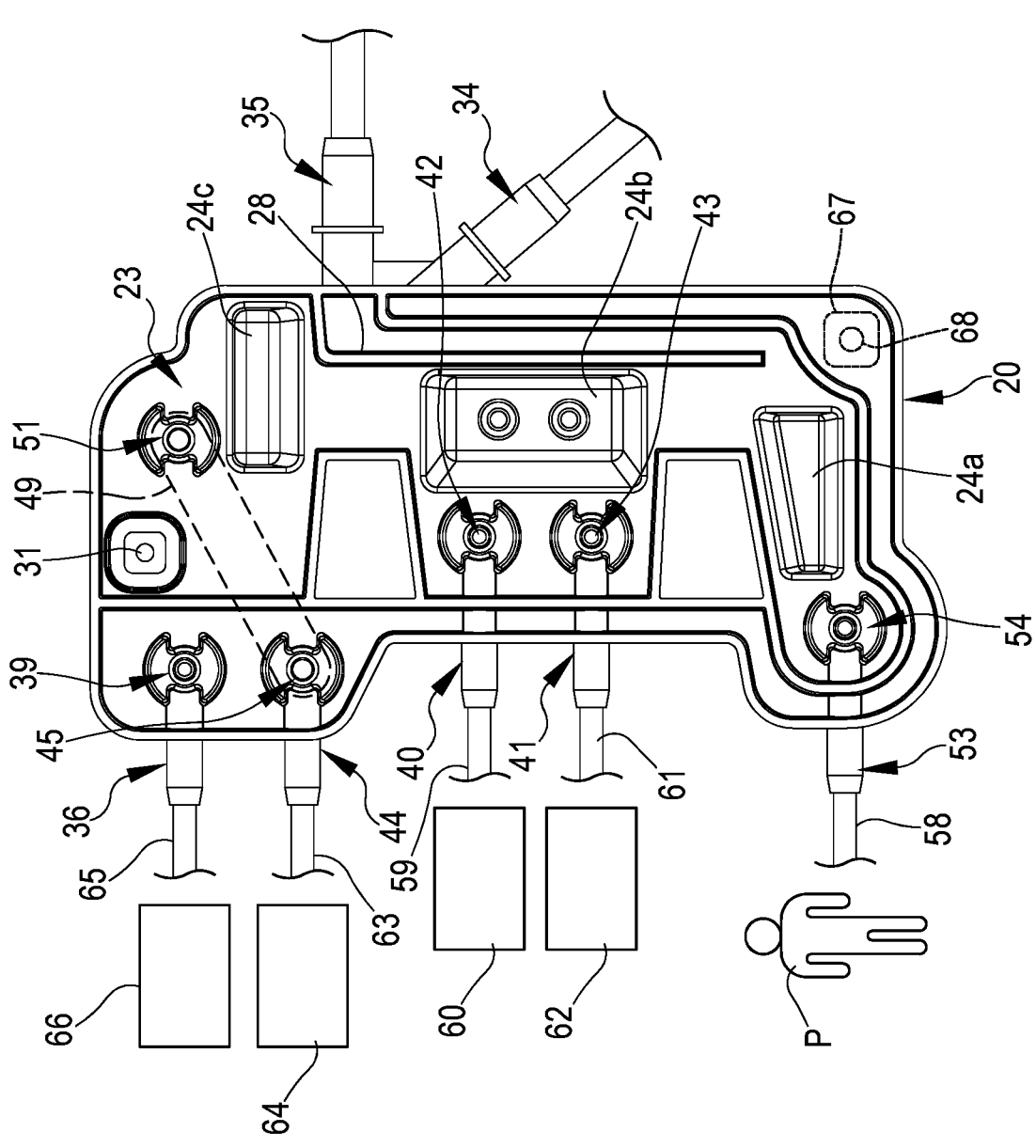
FIG. 16 shows is a rear view of another embodiment of the manifold assembly with some parts removed to illustrate the interior and some other parts schematically represented.
Figure 17:
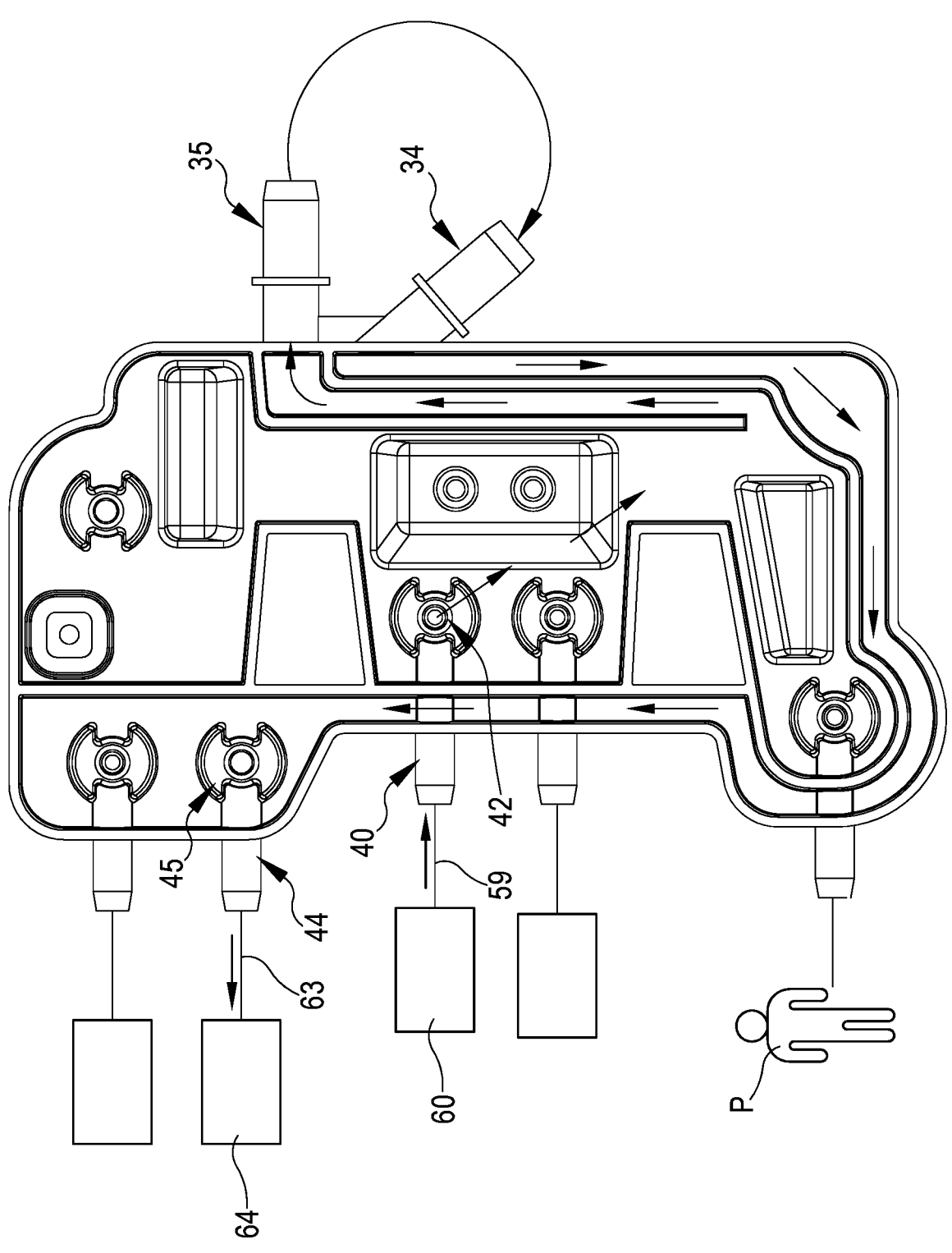
FIG. 17 is the rear view of FIG. 16 illustrating a respective flow configuration.

FIGS. 16 and 17 show another embodiment of the manifold assembly 3 of the peritoneal dialysis apparatus 1 (APD). The cycler 2 of this embodiment is not shown and may have the same structure/architecture disclosed for the first embodiment.

The manifold assembly 3 (FIGS. 16 and 17) that organizes tubing and performs many functions discussed herein is different from the manifold assembly 3 of embodiment 1 in the following features.

As can be seen comparing FIGS. 3 and 16 (the same reference numerals are used for the same elements), the first dialysis port 40 and the second dialysis port 41 open inside the second compartment 23 instead of the first compartment 22. The first dialysis valve 42 and the second dialysis valve 43 are positioned in the second compartment 23 and close to the second expansion chamber 24b.

The first dialysis fluid line tube 59 has the first end connected to the first supply bag 60 and the second end connected to the second compartment 23. The second dialysis fluid line tube 61 has the first end connected to the second supply bag 62 and the second end connected to the second compartment 23.

In addition, the drain port 36 and the drain fluid line tube 65 are arranged close to a top of the casing 19 and, when the manifold assembly 3 is properly mounted on the cycler 2, are located above the heater port 44 and the heater line tube 63.

The second inner septum 28 has a first extremity connected to the right long side of the plastic rigid shell 20, close to the second pump port 35 and, differently from the embodiment of FIG. 3, the area of the second compartment 23 with the hole 31 and the breathable membrane 33 is not separated from the by-pass valve 51 by said second inner septum 28.

Furthermore, the hole 31 and the breathable membrane 33 are next to the top short side of the plastic rigid shell 20.

An area 67 of the plastic sheet 21 is configured to be coupled to displacement sensor 68 (shown only schematically) of the cycler 2 when the manifold assembly 3 is properly mounted on the cycler 2.

FIG. 16 shows that said area 67 faces a zone of the first compartment 22 located at a right bottom elbow the substantially U-shaped first elongated passage. The displacement sensor 68 is mounted on the front panel 13 of the cycler 2.

Figure 10:
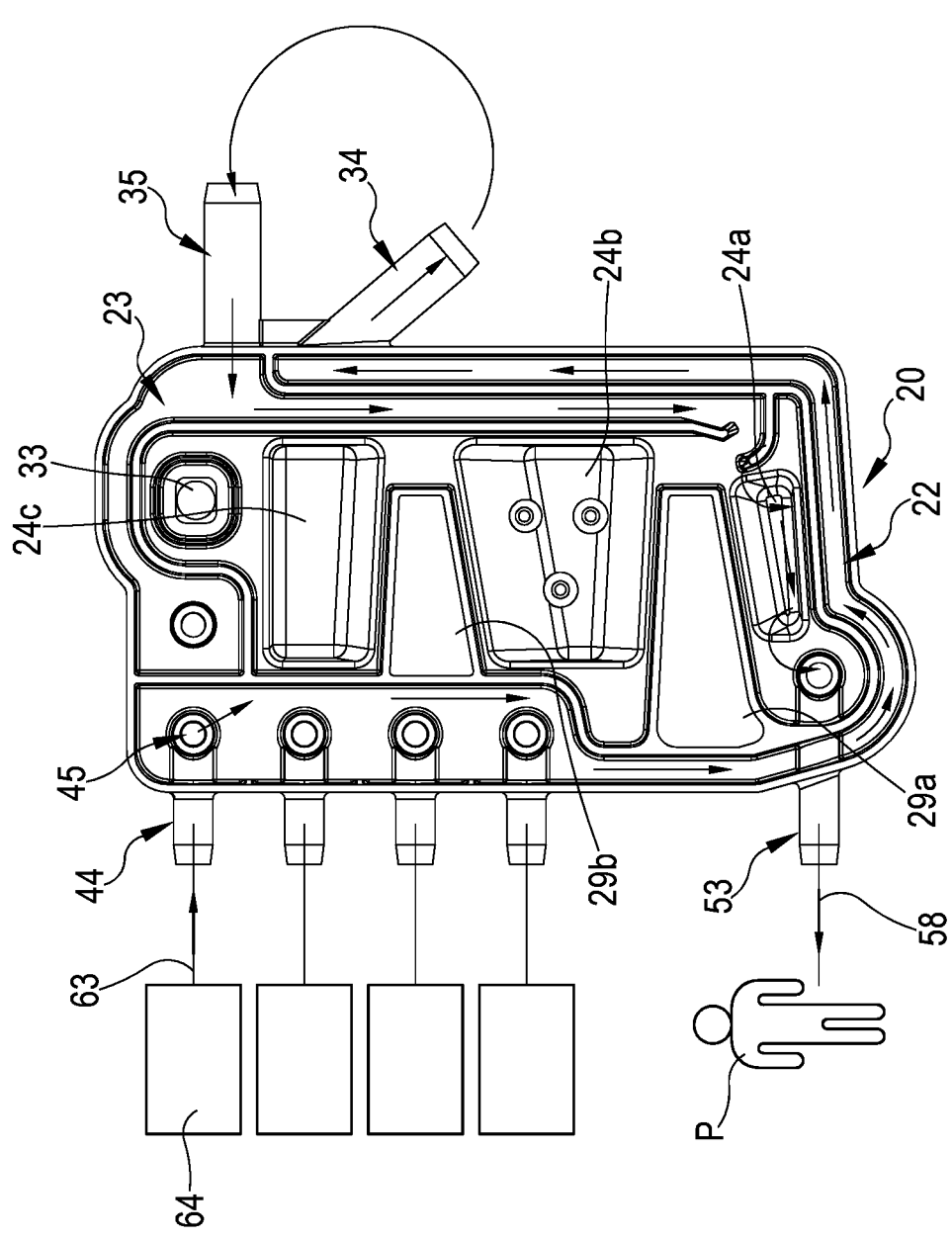
Figure 11:
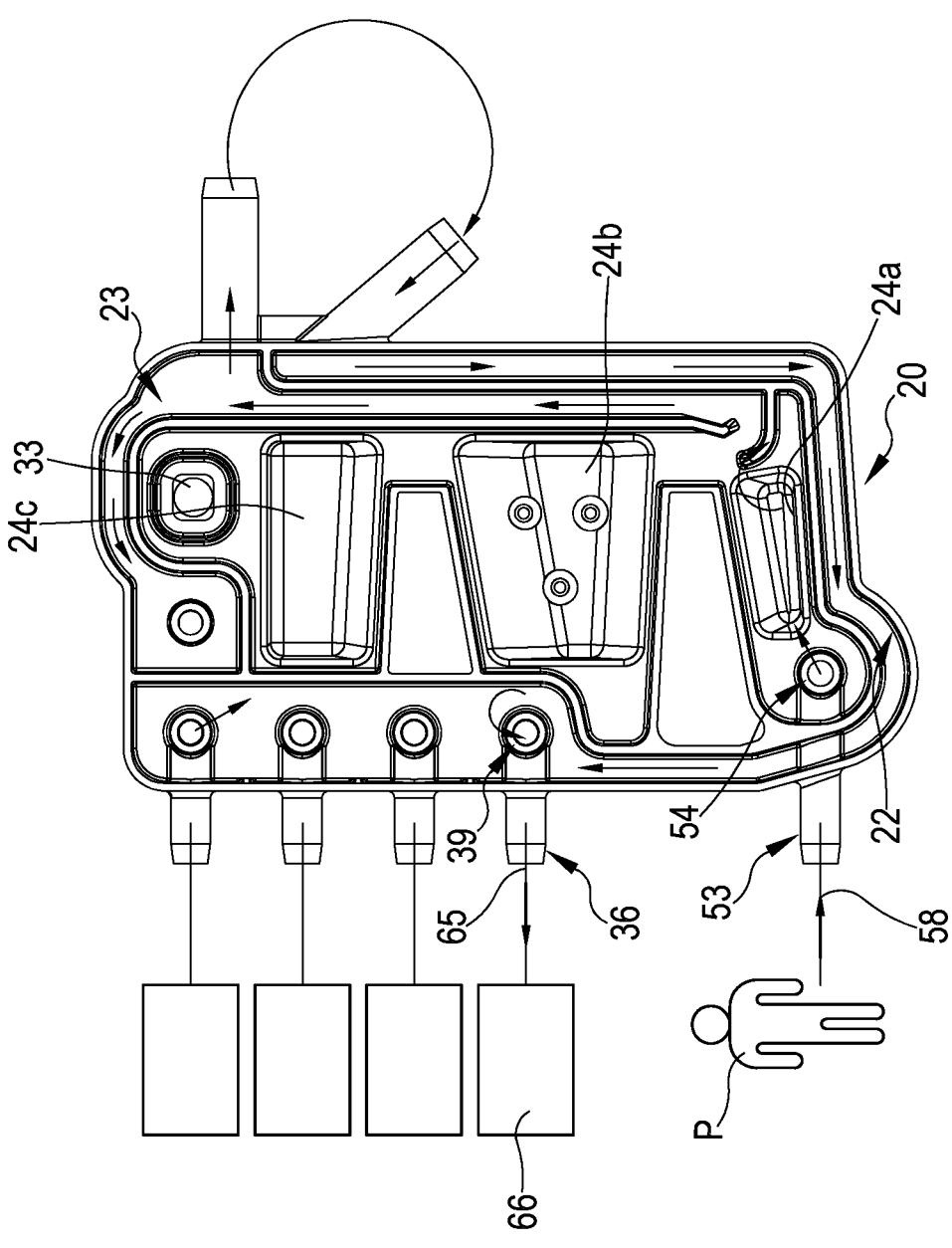

The flow route from the heater bag 64 to the patient P and the flow route from the patient P to drain are the same shown in FIGS. 10 and 11 and disclosed in the previous paragraphs.

Figure 9:
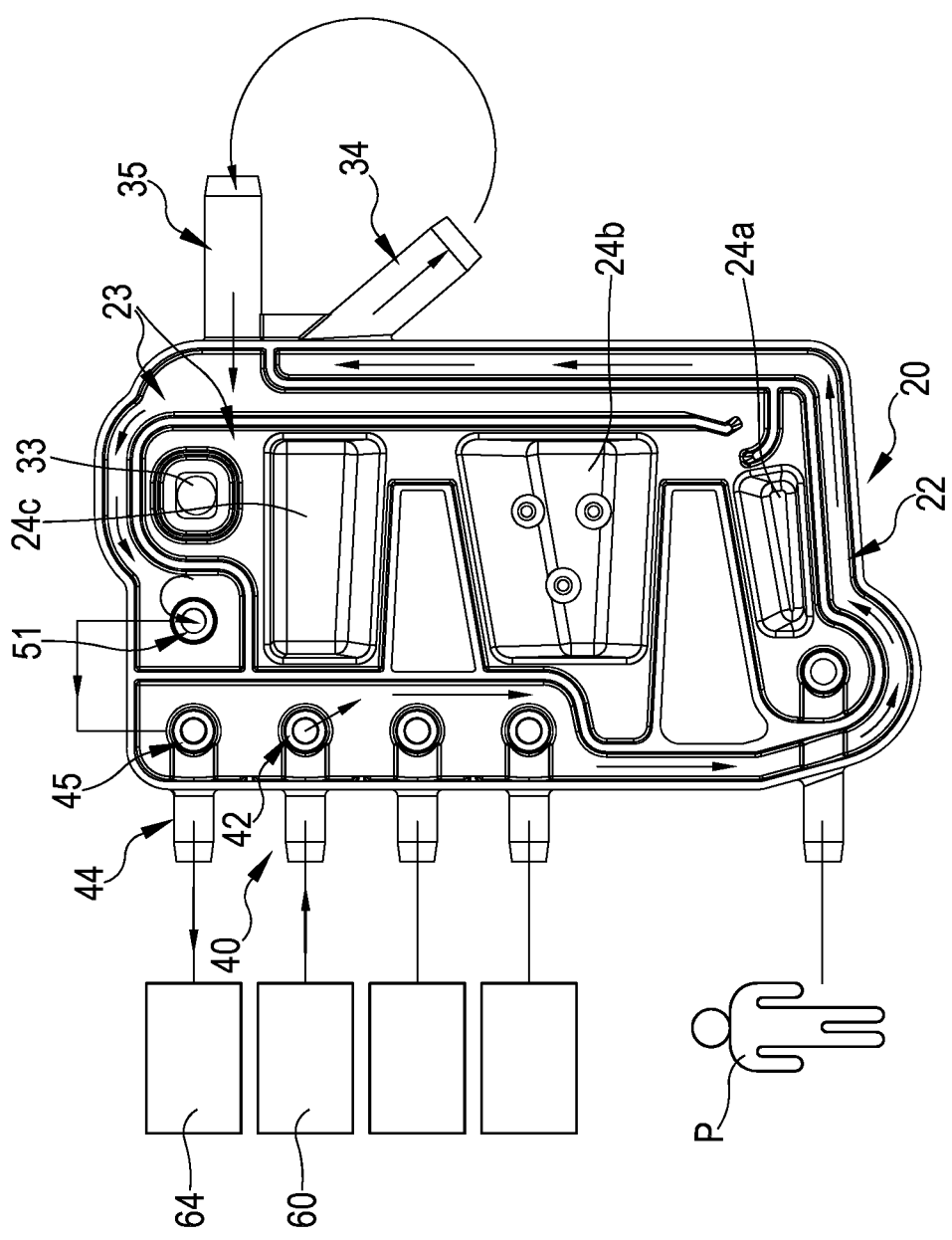

Because of the different position of the first dialysis valve 42 and second dialysis valve 43, the flow route from the first supply bag 60 to the heater bag 64 is other than the one shown in FIG. 9.

Indeed, in this second embodiment (FIGS. 17 and 18), the control unit 5 opens and keeps open the heater valve 45 and the first dialysis valve 42 while closes and keeps closed the by-pass valve 51, the second dialysis valve 43, the drain valve 39 and the patient valve 54. The control unit 5 commands the motor to rotate the peristaltic pump 6 in the second rotation direction (ClockWise in FIG. 9) to pump the dialysis fluid from the second compartment 23 to the first compartment 22.

The treatment sequence for the manifold assembly 3 of the second embodiment is shown in the following table (Table 4).

TABLE 4

| Step | From | To | Valves Open | Pump Direction |
|---|---|---|---|---|
| 1 | First supply bag | Heater bag | Heater valve First dialysis valve | ClockWise |
| 2 | Heater bag | Patient | Heater valve Patient valve | CounterClockWise |
| 3 | Patient | Drain | Drain valve Patient valve | ClockWise |

Before patient treatment, the manifold assembly 3 of the second embodiment is primed. A possible priming sequence is represented in the following table (Table 5).

18

TABLE 5

| Step | From | To | Valves Open | Pump Direction |
|---|---|---|---|---|
| 1 | Heater bag | Drain | By-pass valve Drain valve | ClockWise |
| 2 | First supply bag | Drain | First dialysis valve Drain valve | ClockWise |
| 3 | Second supply bag | Drain | Second dialysis valve Drain valve | ClockWise |
| 4 | Heater bag | Patient | Heater valve Patient valve | CounterClockWise |

Embodiment 3

Figure 19:
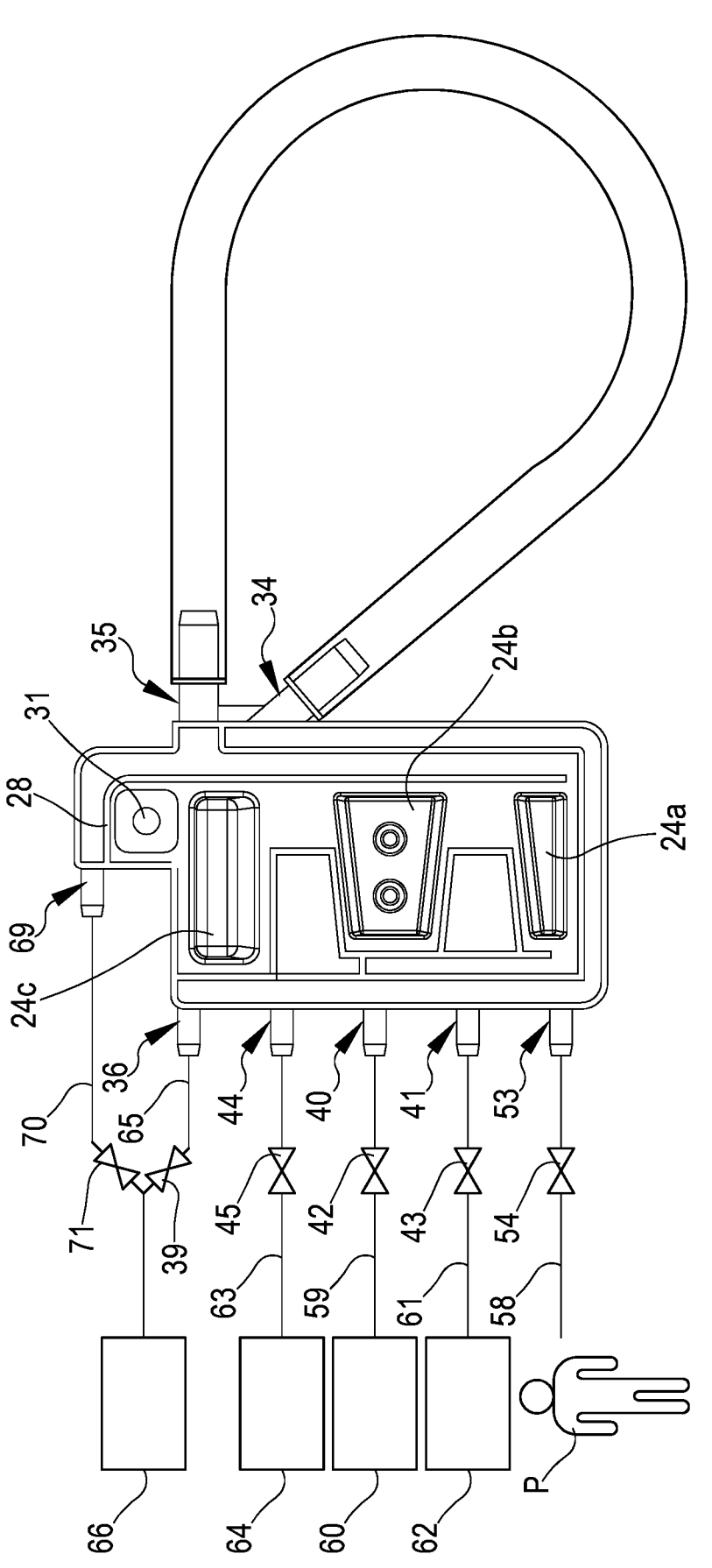
FIG. 19 is a rear view of further embodiment of the manifold assembly with some parts removed to illustrate the interior and some other parts schematically represented.

FIG. 19 shows another embodiment of the manifold assembly 3 of the peritoneal dialysis apparatus 1 (APD). The cycler 2 of this embodiment is different from the first embodiment, because the valves are not part of the casing 7 and the occlusion elements of the cycler 2 are pinch valves.

In this third embodiment, like in the second embodiment, as can be seen comparing FIGS. 3, 16 and 19 (the same reference numerals are used for the same elements), the first dialysis port 40 and the second dialysis port 41 open inside the second compartment 23 instead of the first compartment 22.

All the ports do not comprise valves or part of valves. The drain port 36 and the drain fluid line tube 65 are arranged close to a top of the casing 19, like in the second embodiment.

The second inner septum 28 separates the area of the second compartment 23 with the hole 31 and the breathable membrane from an area of the second compartment 23 with an auxiliary drain port 69 connected to an auxiliary drain fluid line tube 70.

The drain valve 39, first dialysis valve 42, second dialysis valve 43, heater valve 45, patient valve 54 are clamps part of the cycler 2 and operating on tube sections of the drain fluid line tube 65, first dialysis fluid line tube 59, second dialysis fluid line tube 61, heater line tube 63, patient line tube 58. The clamp and the tube section form together a pinch valve.

In addition, an auxiliary drain valve 71 works on the auxiliary drain fluid line tube 70 and the drain fluid line tube 65 merges with the auxiliary drain fluid line tube 70 in a common drain line before reaching the drain 66 (FIG. 19).

The flow route from the heater bag 64 to the patient P and the flow route from the patient P to drain are the same shown in FIGS. 10 and 11 and disclosed in the previous paragraphs (first embodiment).

The flow route from the first supply bag 60 to the heater bag 64 is the same of the second embodiment (see Table 3).

A possible priming sequence is represented in the following table (Table 6).

TABLE 6

| Step | From | To | Valves Open | Pump Direction |
|---|---|---|---|---|
| 1 | Heater bag | Drain | Heater valve Auxiliary drain valve | CounterClockWise |
| 2 | First supply bag | Drain | First dialysis valve Drain valve | ClockWise |
| 3 | Second supply bag | Drain | Second dialysis valve Drain valve | ClockWise |
| 4 | Heater bag | Patient | Heater valve Patient valve | CounterClockWise |

Valves

Figure 20C:
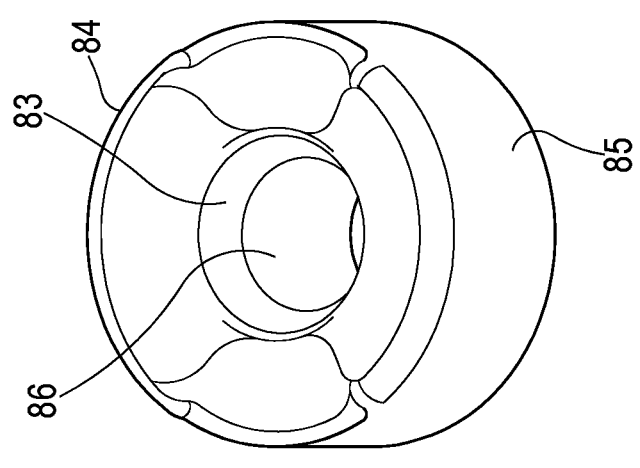
FIGS. 20A, 20B and 20C show embodiments of the valves of the embodiment of FIGS. 16, 17 and 18.
Figure 20B:
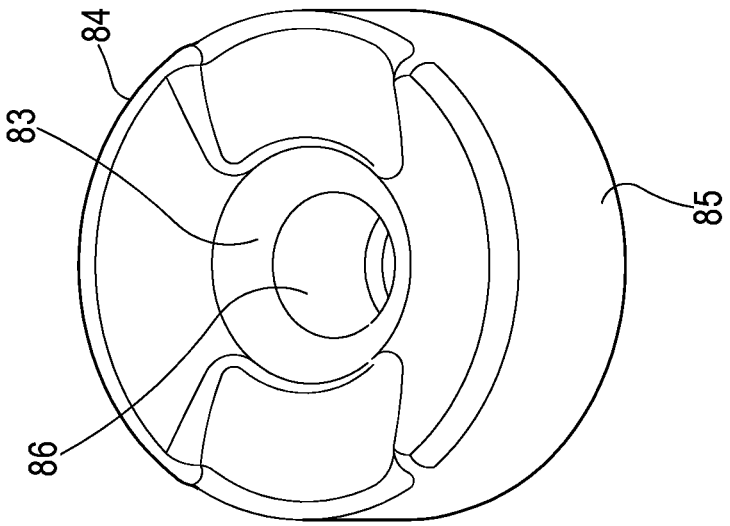
Figure 20A:
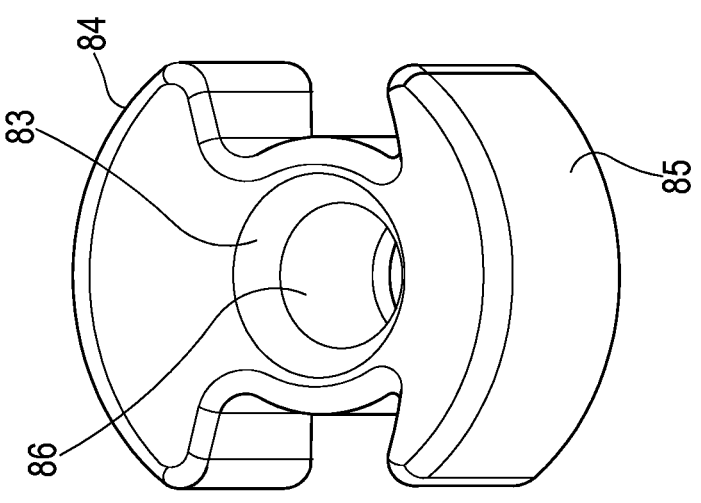

In some embodiments, the valves are part of the casing and are shaped like in FIGS. 20A, 20B, 20C. For instance, all the valves (drain valve 39, first dialysis valve 42, second dialysis valve 43, heater valve 45, by-pass valve 51, patient valve 54) of embodiment two of FIGS. 16 and 17 are of the type shown in FIG. 20A.

This kind of valves is configured to work with the occlusion element 7 illustrated in FIGS. 21A, 21B, 21C, 21D, 22 and 23.

The occlusion element 7 comprises the plunger 15, like the one of FIGS. 6A, 6B and 7, and further comprises a mechanical tensioning plunger 76. Both the plunger 15 and the tensioning plunger 76 are mechanically coupled to an actuator 73, shown in FIGS. 22 and 23.

Figure 22A:
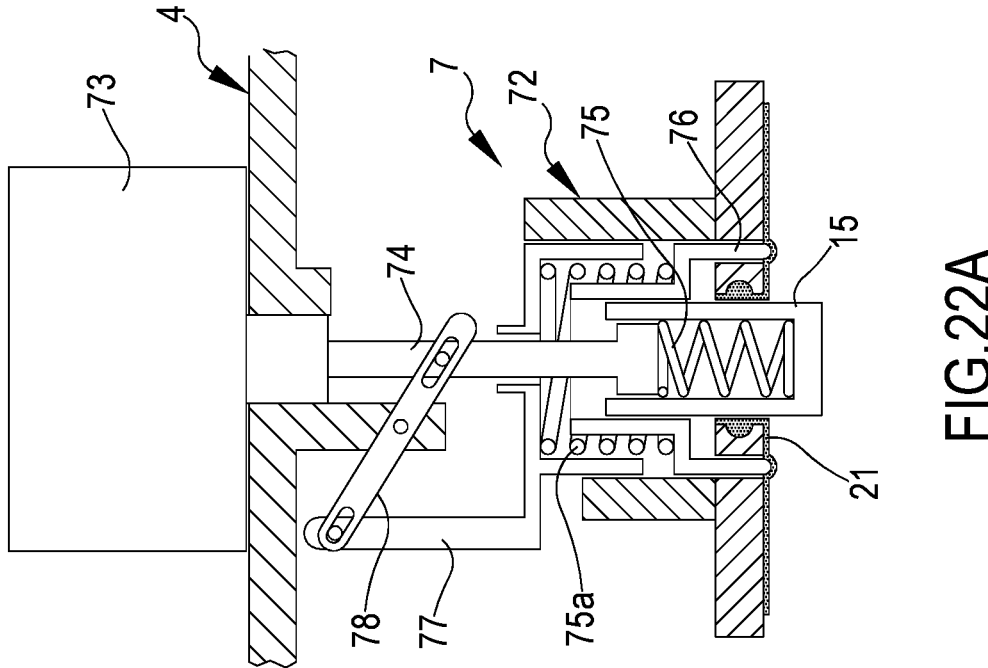
FIG. 22A is a variant of the embodiment of FIG. 22.
Figure 22:
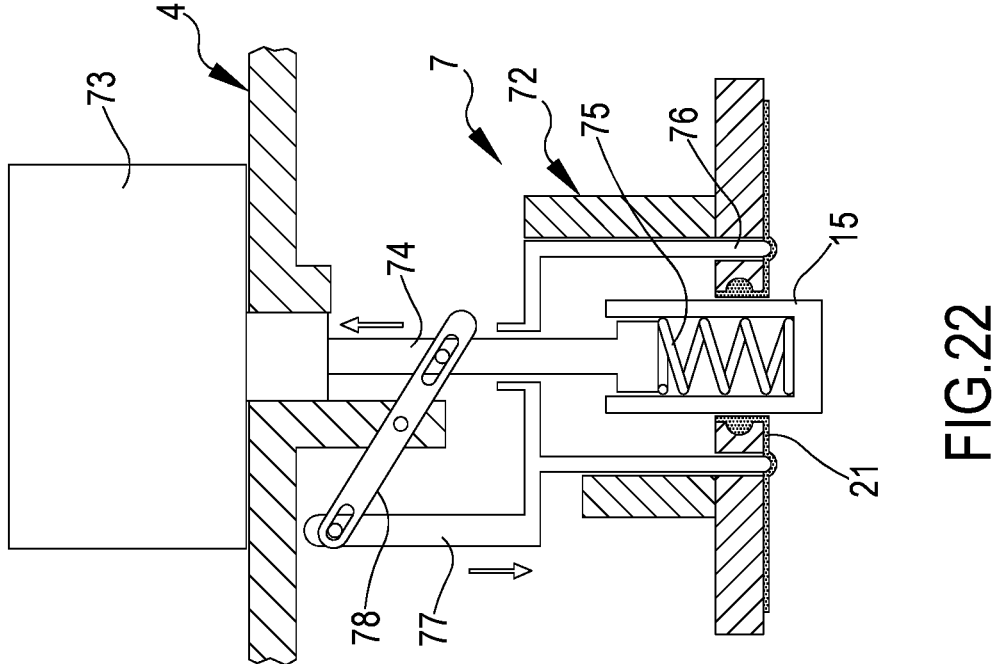
FIG. 22 is an embodiment of the element of FIG. 21A.

In the embodiment of FIG. 22, the actuator 73 is a linear actuator connected to a shaft 74. A distal end of the shaft 74 carries the plunger 15 and a damping and/or resilient element 75 (like a spring) is placed between the distal end and said plunger 15. The plunger 15 is shaped like a cup housing the spring.

The damping and/or resilient element 75 allows to reduce the force exerted on the membrane 21 to avoid damaging said membrane 21.

Like in FIGS. 16 and 17, the actuator 73 is configured to move the plunger 15 along an axial direction and between the retracted position, in which the plunger 15 is spaced from the soft membrane 21 and the port is open, and a forward position, in which the plunger 15 is at least in part accommodated in the seat and the soft membrane 21 is deformed and trapped between said plunger 15 and said seat to close the port.

The membrane tensioner 72 is configured to raise the soft membrane 21 away from the seat when the plunger 15 goes back to the retracted position and to counteract a possible negative pressure tending to keep the valve closed.

The membrane tensioner 72 comprises a tensioning plunger 76 which is also mechanically connected to the actuator 73. The tensioning plunger 76 is shaped substantially like a cylinder, is coaxial to the plunger 15 and surrounds at least in part the plunger 15.

Figure 24:
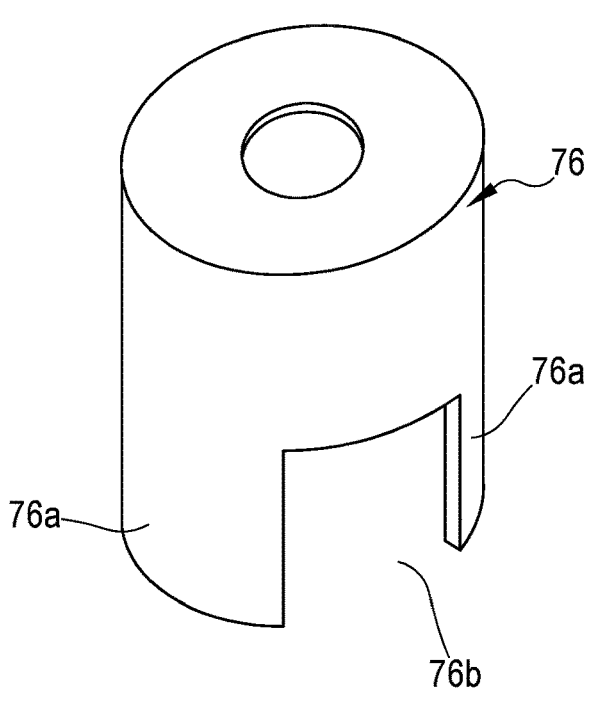
FIG. 24 shows a member of the element of FIG. 22 or 23.

The tensioning plunger 76 comprises two arched walls 76a coaxial to a central axis. The walls 76a are spaced one from the other to delimit two windows 76b between them (FIGS. 24 and 25).

The tensioning plunger 76 is fitted on the shaft 74 and is axially movable along said shaft 74. Borders of the arched walls 76a of the tensioning plunger 76 face the soft membrane 21 and the plunger 15 may protrude from the tensioning plunger 76.

The actuator 73 is also configured to move the tensioning plunger 76 between a retracted position, in which the tensioning plunger 76 is spaced from the soft membrane 21, and a forward position, in which the tensioning plunger 76 engages the soft membrane 21 at locations other than an edge of the seat, to move away the soft membrane 21 from the edge and to stretch said soft membrane 21 above the seat.

In other embodiments, not shown, the tensioning plunger 76 may be moved by an auxiliary actuator, not shown.

The actuator 73 is housed in the box 4 of the cycler 2; the plunger 15, the tensioning plunger 76 and the shaft 74 are guided through openings fashioned in the box 4 of the cycler 2.

Figure 21C:
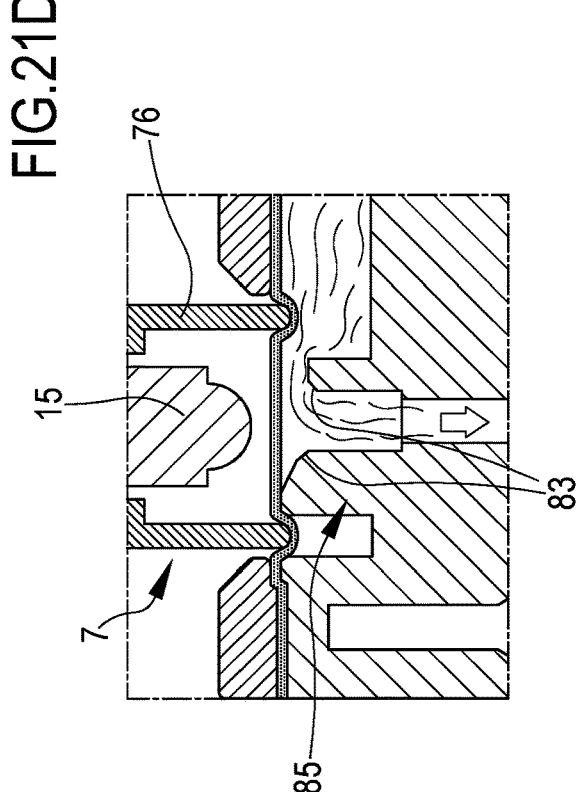
FIGS. 21A to 21D show working steps of the valve of FIG. 20A cooperating with an element of the cycler.
Figure 21D:
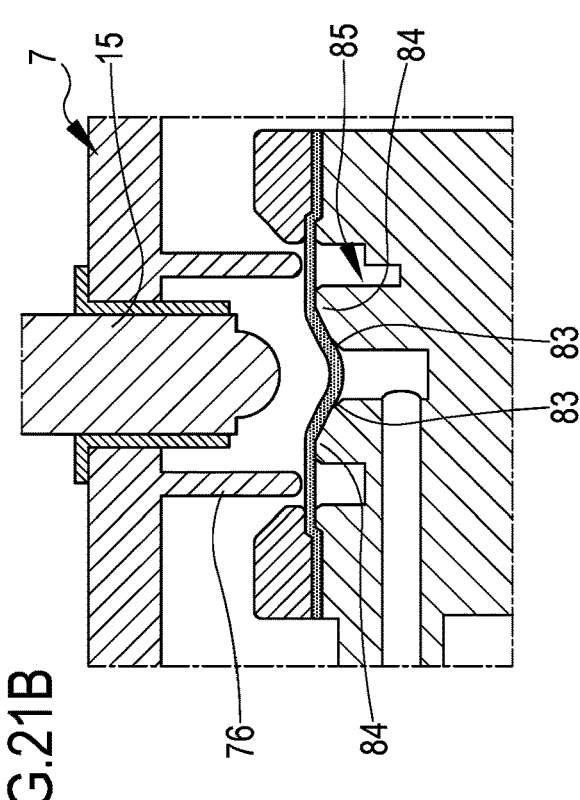
Figure 21A:
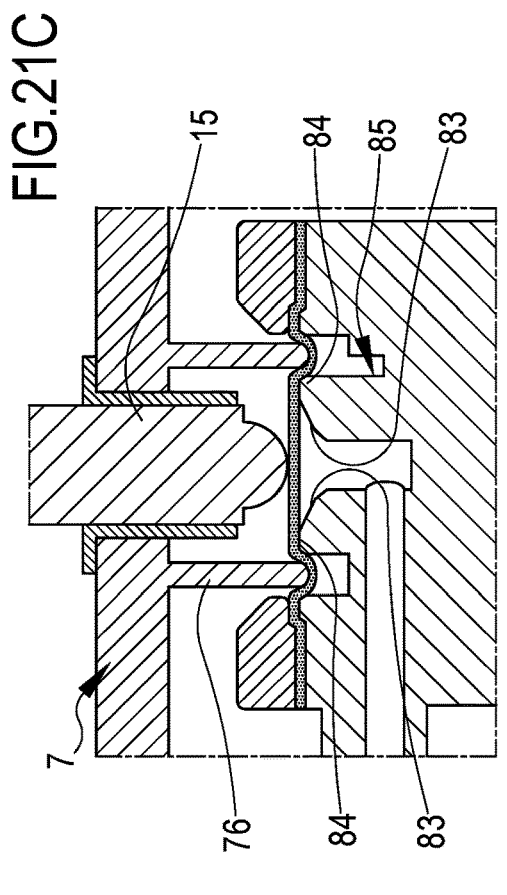
Figure 21B:
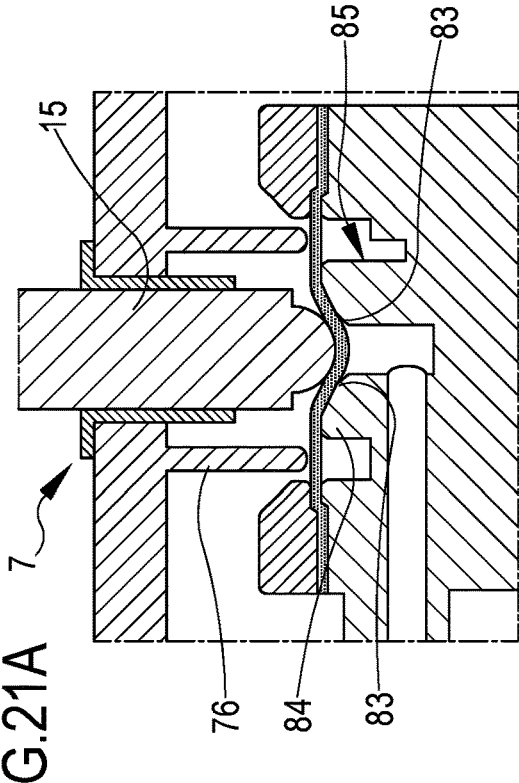

The tensioning plunger 76 is in the retracted position when the plunger 15 is in the forward position (FIGS. 21A and 21B). In this configuration, the plunger 15 protrudes from the tensioning plunger 76.

The tensioning plunger 76 is in the forward position when the plunger 15 is in the retracted position (FIGS. 21C and 21D). In this configuration, the plunger 15 is entirely housed within the tensioning plunger 76 and does not protrude beyond the borders of the tensioning plunger 76.

The occlusion element 7 comprises a reverse mechanism connecting the tensioning plunger 76 and the plunger 15. The reverse mechanism is configured to move the plunger 15 in an opposite direction with respect to a moving direction of the tensioning plunger 76 when the plunger 15 is moved by the actuator 73.

In the embodiment of FIG. 22, the tensioning plunger 76 comprises a projection 77 extending parallel to the shaft 74 and a rocker lever 78. A first end of the rocker lever 78 is hinged to the shaft 74 of the plunger 15, a second end of the rocker lever 78 is hinged to the projection 77 of the tensioning plunger 76 and a middle portion of the rocker lever 78 is hinged to a stationary part of the cycler 2, for instance to a part of the box 4.

When the linear actuator moves the plunger 15 towards the forward position, the rocker lever 78 tilts and moves the tensioning plunger 76 towards the retracted position. When the linear actuator moves the plunger 15 towards the retracted position, the rocker lever 78 tilts and moves the tensioning plunger 76 towards the forward position.

The variant embodiment of FIG. 22A comprises an additional damping and/or resilient element 75a (a spring) coupled to the tensioning plunger 76. In this embodiment, the cylinder defining the tensioning plunger 76 is in two parts. A first part is rigidly connected to the projection 77. A second part carries the borders of the arched walls 76a of the tensioning plunger 76 facing the membrane 21. The additional damping and/or resilient element 75a is interposed between the first and the second part.

The additional damping and/or resilient element 75a allows to reduce the force exerted on the membrane 21 by the tensioning plunger 76, to avoid damaging said membrane 21. A further function of the additional damping and/or resilient element 75a is to compensate for possible plastic deformation of the membrane 21 that may lose elasticity and may plastically deform over time. Even if the membrane 21 is plastically stretched, the additional damping and/or resilient element 75a is always able to push the borders of the arched walls 76a of the tensioning plunger 76 against the membrane 21 (forward position), to move away said soft membrane 21 from the edge and to stretch said soft membrane 21 above the seat.

Figure 23:
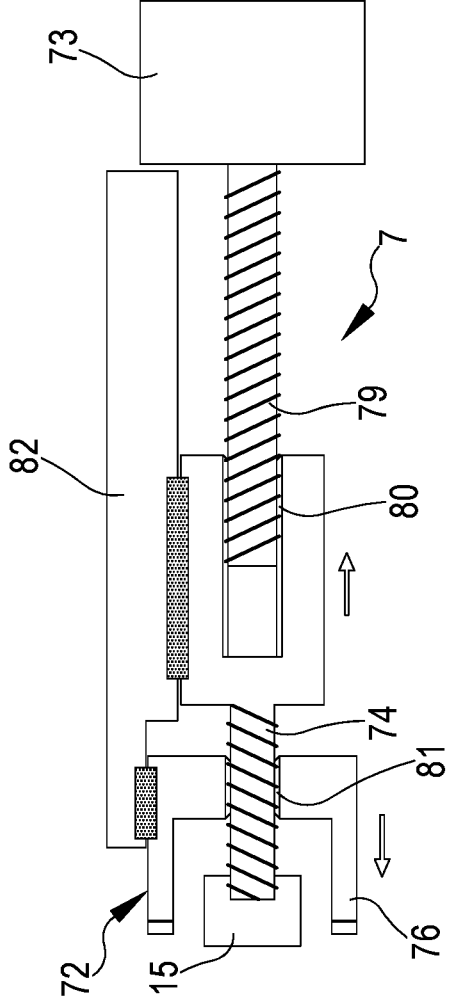
FIG. 23 shows another embodiment of the element of FIG. 21A.

In the embodiment of FIG. 23, the actuator 73 is a stepper motor comprising a rotatable shaft 79 connected to the shaft 74 of the plunger 15. The rotatable shaft 79 has an outer thread and is coupled, through a left hand threaded coupling 80, to an inner thread of the shaft 74.

The shaft 74 has an outer thread and is coupled, through a right hand threaded coupling 81, to an inner thread of the tensioning plunger 76.

The tensioning plunger 76 and the shaft 74 are axially guided by a stationary element 82, for instance to a part of the box 4.

The rotation of the rotatable shaft 79 caused by the stepper motor makes the shaft 74 moving only axially in a first direction (the shaft 74 does not revolve), e.g. towards the forward position of the plunger 15.

Because of the left hand threaded coupling 80, the axial movement of the shaft 74 drives the rotation of the tensioning plunger 76 and, due to a different pitch of the left hand threaded coupling 80 and right hand threaded coupling 81, also the axial movement of said tensioning plunger 76 in a second direction, opposite the first direction, e.g. towards a retracted position of the tensioning plunger 76.

When the stepper motor moves the plunger 15 towards the forward position, the left hand threaded coupling 80 and right hand threaded coupling 81 work to move the tensioning plunger 76 towards the retracted position. When the stepper motor moves the plunger 15 towards the retracted position, the left hand threaded coupling 80 and right hand threaded coupling 81 work to move the tensioning plunger 76 towards the forward position.

In order to properly work with the plunger 15 and with the membrane tensioner 72, the valve has a circular edge 83 delimiting the seat and also an auxiliary edge 84 extending in part around the circular edge 83 and spaced with respect to said edge 83.

Instead of the hollow barrel 38 of FIGS. 6A, 6B and 7, the valve comprises a shaped member 85 which protrudes from the bottom surface of the respective compartment 22, 23 and comprises the edge 83 and the auxiliary edge 84.

The shaped member 85 is substantially cylindrical and delimits a central cylindrical cavity 86. The edge 83 delimits an upper part of said cavity 86 and the auxiliary edge 84 comprises two arch shaped parts coaxial to the cavity and to the edge 83.

As shown in FIGS. 20A to 21D, the auxiliary edge 84 is raised with respect to the edge 83 such that, when the manifold assembly 3 is properly mounted on the site 14 of the cycler 2, the auxiliary edge 84 is closer to the occlusion element than the edge 83.

FIGS. 21A to 21D show working steps of the assembly comprising the valve and the occlusion element 7.

In FIG. 21A, the valve is closed. The plunger 15 is in the forward position and in part accommodated in the seat, the soft membrane 21 is trapped between said plunger 15 and the edge 83.

In FIG. 21B, the valve is still closed even if the plunger 15 is partly raised, because of negative pressure which keeps the soft membrane 21 against the edge 83.

In FIG. 21C, the valve is open, because the tensioning plunger 76 in the forward position partly surrounds the shaped member 85 and the auxiliary edge 84 and pulls the soft membrane 21 against the auxiliary edge 84. This way, the soft membrane 21 is detached from the edge 83.

In this position, the shaped member 85 is at least in part positioned inside the tensioning plunger 76. Each arched wall 76a of the tensioning plunger 76 is placed close to one of the two arch shaped part of the auxiliary edge 84 and radially outside said arch shaped part of the auxiliary edge 84, as shown in FIG. 25.

The windows 76b face radial openings delimited between the arched walls 76a and allow fluid communication between the cylindrical cavity 86 and the first or second compartment 22, 23, therefore the valve is open (FIG. 21D).

The structure of valve and occlusion element 7 just disclosed may be also part of other kind of medical apparatuses (e.g. dialysis apparatuses for extracorporeal treatment of blood), not necessarily of the peritoneal dialysis apparatus disclosed above.

The medical apparatus may comprise a dialysis machine and a manifold assembly and the manifold assembly is mounted or mountable on the dialysis machine.

The manifold assembly comprises a casing comprising a rigid shell and at least one soft membrane, the rigid shell and soft membrane delimit at least a first fluid passage. The rigid shell comprises at least one port in fluid communication with the first fluid passage and with a second fluid passage. The at least one port has a seat and the soft membrane facing the seat.

The dialysis machine comprises at least one occlusion element 7 which, when the manifold assembly is properly mounted on the dialysis device, faces the seat with the soft membrane 21 there between. The seat is configured for accommodating, at least partially, a respective occlusion element 7 of the dialysis machine.

The dialysis apparatus may be an apparatus for extracorporeal treatment of blood comprising: a blood treatment device; an extracorporeal blood circuit coupled to the blood treatment device; a blood pump, wherein a pump section of the extracorporeal blood circuit being configured to be coupled to the blood pump; a treatment fluid circuit operatively connected to the extracorporeal blood circuit and/or to the blood treatment device. The treatment fluid circuit comprises a dialysis line connected to a fluid chamber of the treatment unit and a fluid evacuation line connected to the fluid chamber. The treatment fluid circuit comprises an infusion circuit comprising one or more infusion lines of a replacement fluid. The manifold assembly may be part of the extracorporeal blood circuit or of the treatment fluid circuit.

Calibration

The manifold assembly 3 described above may be used to calibrate the peristaltic pump 6, i.e. to estimate the stroke liquid volume of the yielding pump tube 55 connected to the peristaltic pump 6 in order to reach volumetric accuracy measure requirements.

The following description is referred to the manifold assembly 3 of the second embodiment of FIGS. 16 and 17. This embodiment is illustrated also in FIGS. 25 and 26. The upper part of the second compartment 23 and the air buffer volume are in fluid communication, through the hole 31, the breathable membrane 33 and an air filter 88, with an auxiliary chamber 87 part of the cycler 2. The pressure transducer 10 is connected to the auxiliary chamber 87 and an air valve 89 allows to open or close communication of the auxiliary chamber 87 with ambient air.

The peristaltic pump 6 comprises an encoder or is coupled to an encoder, not shown in the attached Figures. The encoder is operatively connected to the control unit 5 and is configured to detect the position and movement of the pressing rollers 6a of the peristaltic pump 6.

The control unit 5 is operatively connected the motor of the peristaltic pump 6, to the first level sensor 8, to the second level sensor 9, to the air valve 10, to the actuators of the occlusion elements 7 and to the pressure transducer 10 and is configured and/or programmed to calibrate the peristaltic pump 6 according to the method here detailed.

Figure 26:
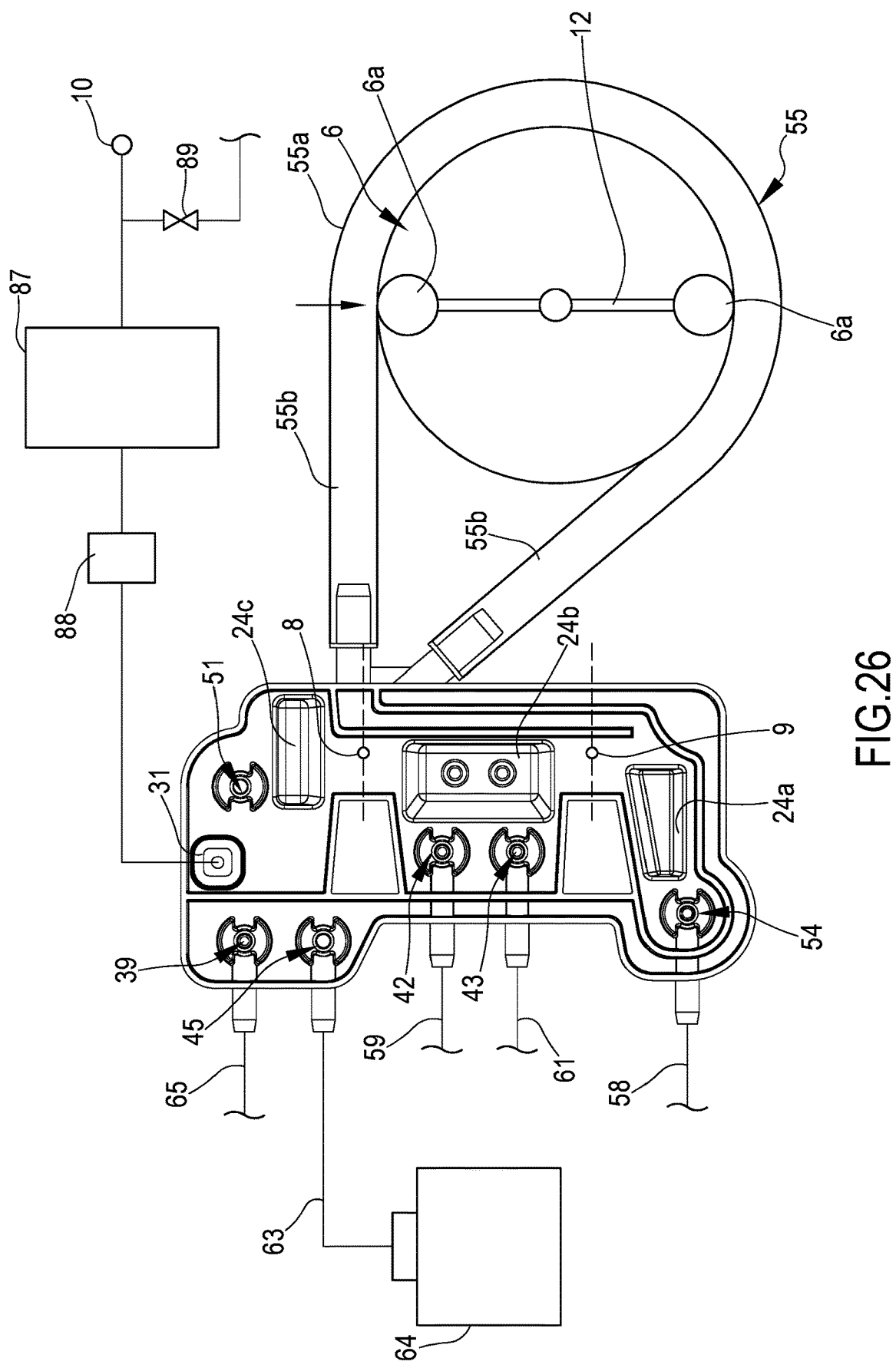
FIG. 26 shows the manifold assembly of FIGS. 16 and 17 configured to perform a method of calibration.

As shown in FIG. 26, the first level sensor 8 or high level sensor and the second level sensor 9 or low level sensor, delimit a high level "C" and a low level "A" in the second compartment 23.

A first volume "V1" is delimited in the second compartment 23 below the low level "A". The first volume "V1" is about 10 ml. A second volume "V2" is delimited in the second compartment 23 between the low level "A" and the high level "C". The second volume "V2" is between two and four times a nominal stroke liquid volume of the peristaltic pump 6. The nominal stroke liquid volume of the peristaltic pump 6 may be 7 ml and the second volume "V2" is about 21 ml. A third volume "V3" is delimited in the second compartment 23 above the high level "C". The third volume "V3" is about 15 ml. The auxiliary chamber 87 delimits inside a fourth volume "V4" of a about 26 ml. A sum of the second, third and fourth volume is about 62 ml.

The yielding pump tube 55 shaped as a loop comprises a rounded part 55a and two straight parts 55b. The rounded part 55a and two straight parts 55b form a single tube. The straight parts 55b are respectively connected to the first pump port 34 and the second pump port 35. The rounded part 55a is configured to be pressed and deformed/squeezed by the pressing rollers 6a of the peristaltic pump 6.

Looking at FIG. 25, if the peristaltic pump 6 rotates counterclockwise, each of the two pressing rollers 6a starts squeezing the rounded part 55a at a bottom portion, between the rounded part 55a and the lower of the two straight parts 55b, and releases the rounded part 55a at a top portion, between the rounded part 55a and the upper of the two straight parts 55b.

In order to calibrate the peristaltic pump 6, i.e. to estimate the stroke liquid volume of the yielding pump tube 55, the following procedure is performed (reference is made to FIGS. 25 to 28).

The drain valve 39, first dialysis valve 42, second dialysis valve 43, by-pass valve 51, patient valve 54 are closed. The heater valve 45 is open and the heater bag 64 is filled with water. The air valve 89 is open.

The control unit 5 controls the peristaltic pump 6 to start rotating counterclockwise, to pump water from the heater bag 64 into the first compartment 22 and then into the second compartment 23. When the low level sensor 9 detects water ($A^{II}$ in FIG. 27), the peristaltic pump 6 is stopped.

Figure 27:
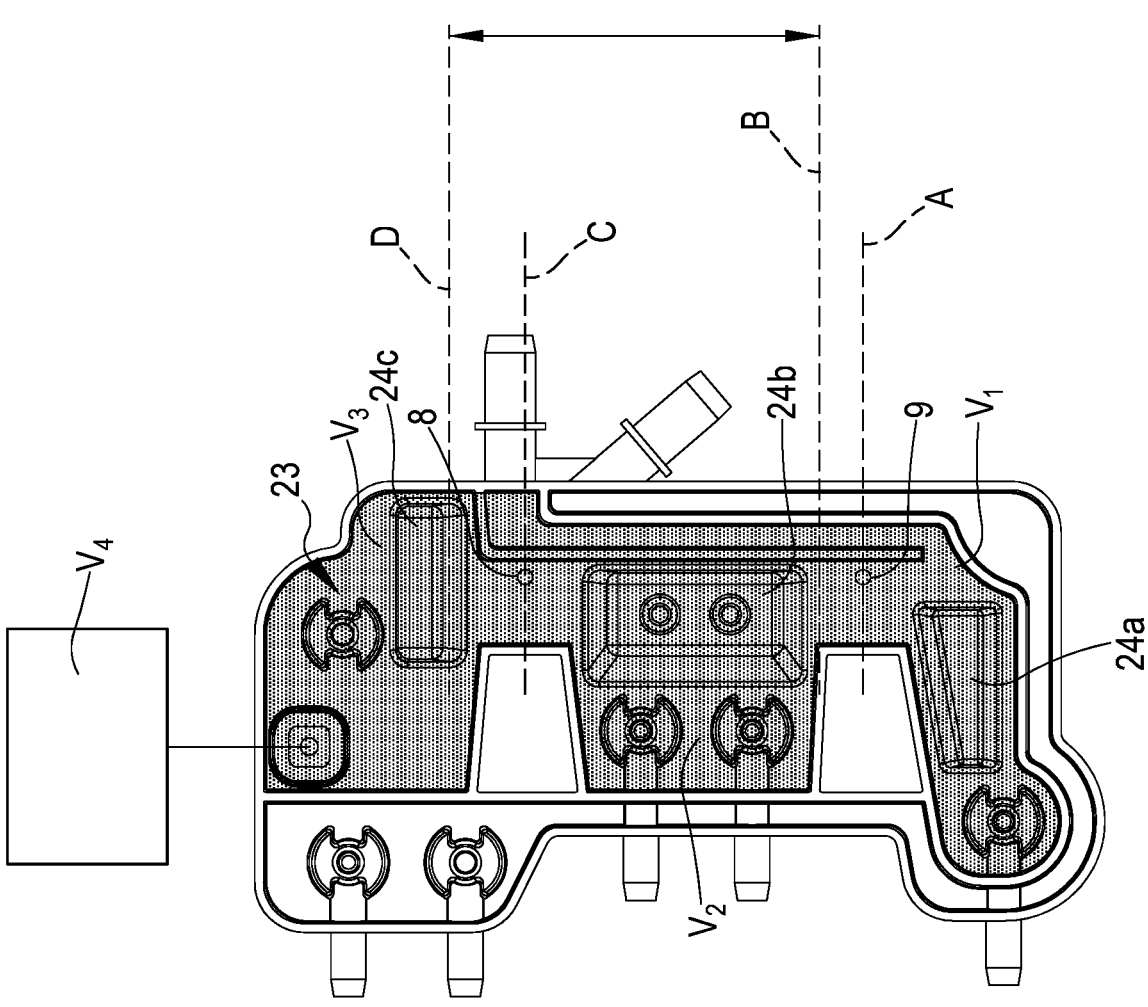
FIG. 27 shows the manifold assembly of FIG. 26 and liquid levels in the manifold during calibration.
Figure 28:
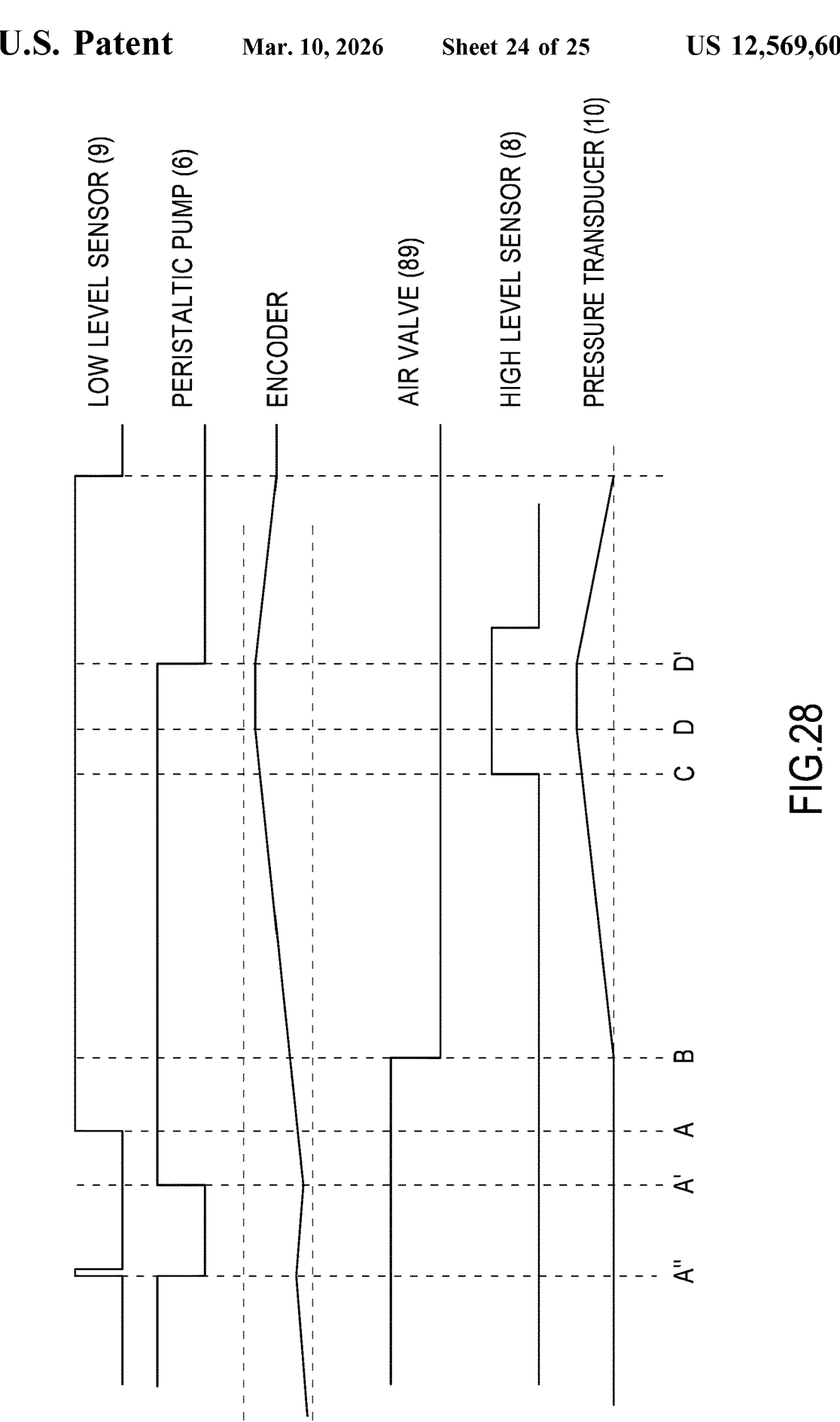
FIG. 28 is a chart showing the method of calibration.

The peristaltic pump 6 is then rotated clockwise to lower the water level until water is no more detected by the low level sensor 9 and then stopped again ($A^{I}$ in FIG. 27).

The peristaltic pump 6 is again rotated counterclockwise. When the low level sensor 9 detects again water (low liquid level A in FIGS. 26 and 27), the control unit 5 controls the peristaltic pump 6 to keep rotating counterclockwise and pumping water in the second compartment 23. Meanwhile, the control unit 5 starts counting encoder pulses starting from the detection of water by the low level sensor 9.

When a predetermined number of pulses "Delta_Encoder_Pulses" (e.g. 280 pulses), corresponding to a predetermined angle of rotation "Delta" (e.g. 105°) of the peristaltic pump 6, is reached and the water level is at a first level B (FIGS. 26 and 27), the air valve 89 is closed and the peristaltic pump 6 to keeps on rotating counterclockwise to pump more water in the second compartment 23 and to compress air in the volume above the water level.

The position of one of the two pressing rollers 6a at the end of the predetermined angle "Delta" of rotation is a predetermined position. Such predetermined position may be at a portion of the yielding pump tube 55 between the rounded part 55a and one of the two straight parts 55b. The water level when the pressing roller 6a is in the predetermined position is the first level B. An extra volume "Extra_Volume" of water is pumped to raise the level from the low liquid level A to the first level B (FIGS. 26 and 27).

Starting from said predetermined position of the peristaltic pump 6 and from the first level B, the control unit 5 rotates the peristaltic pump 6 of a counterclockwise predetermined rotation "Rotor_rev" defined by "n" half-revolutions of the peristaltic pump 6, where "n" is an integer (e.g. n=7). The rotational speed of the peristaltic pump 6 may be 5 rpm.

This way, at the end of the "n" half-revolutions, the same pressing roller 6a is positioned again in the predetermined position and the water level is raised to a second level D.

Since the pressing roller 6a passes in the predetermined position several times during the "n" half-revolutions, the water level is sensed through the high level sensor 8 and the rotation of the peristaltic pump 6 is stopped when the pressing element 6a is in the predetermined position for a first time after sensing the high level C (FIGS. 26 and 27).

Air pressure in the second compartment 23 is measured by the pressure transducer 10. An initial pressure $P_{Init}$ before air compression (first level B) and a final pressure $P_{Final}$ after air compression (second level D) are taken. The initial pressure $P_{Init}$ is about 0 mmHg (differential pressure with respect to atmospheric pressure) and the final pressure is about 400 mmHg.

After stopping the rotation of the peristaltic pump 6 and before taking the final pressure $P_{Final}$, it is provided for waiting for a stabilizing time and keeping on measuring pressure ($D^{I}$ in FIG. 27), to check for possible leakages.

A variation of liquid volume "Vol_Moved" in the second compartment 23, due to the rotation of the peristaltic pump 6 of the predetermined rotation "Rotor_rev", is then calculated as a function of an initial air volume "Compensated_Volume" above the first level B and of the initial pressure $P_{Init}$ and the final pressure $P_{Final}$.

The initial air volume "Compensated_Volume" is a difference between a volume of air above the low liquid level "A" (i.e. V2+V3+V4) and the extra volume of water "Extra_Volume", wherein the extra volume of water "Extra Volume" is the volume of water between the first level B and the low liquid level A, i.e. the volume of water moved by the rotation "Delta" of the peristaltic pump 6.

The stroke liquid volume "Stroke_Vol_Press" of the peristaltic pump 6 is calculated as a ratio between the variation of liquid volume "Vol_Moved" and the "n" half-revolutions of the peristaltic pump 6. The calculation of the stroke liquid volume "Stroke_Vol_Press" as disclosed may be executed consecutively two to five times and an average stroke liquid volume is determined.

The method of calibration may also be implemented in other medical apparatuses comprising a medical machine provided with a peristaltic pump and comprising a manifold assembly, for instance in an apparatus for extracorporeal treatment of blood of the kind above disclosed.

The procedure detailed above may be summarized through the following formulas.

$$Vol\_Extra = 2*(Delta\_Encoder\_Pulses/m)*Stroke\_Vol\_Press \qquad \text{a.}$$

$$Compensated\_Volume = ((V2+V3+V4)-Vol\_Extra) \qquad \text{b.}$$

$$Vol\_Moved = Compensated\_Volume*((Pressure\_Final-Pressure\_Init)/Pressure\_Final) \qquad \text{c.}$$

$$Rotor\_rev = (Zc-Yc)/m \qquad \text{d.}$$

$$Stroke\_Vol\_Press = 2*(Vol\_Moved/Rotor\_rev \qquad \text{e.}$$

$$Stroke\_Vol\_Press = 2*(m/(Zc-Yc))*((V2+V3+V4)-(Delta\_Encoder\_Pulses/2m*Stroke\_Vol\_Press))*((Pressure\_Final-Pressure\_Init)/Pressure\_Final)) \qquad \text{f.}$$

Stroke_Vol_Press may be calculated from equation f., wherein:

| | |
|---|---|
| Stroke_Vol_Press | Ratio between the variation of liquid volume "Vol_Moved" (B to D in FIG. 26) and the "n" half-revolutions of the peristaltic pump 6 between the predetermined positions before the air compression (first level B) and after air compression (second level D). |
| m | Number of pulses (e.g. 480 pulses) measured by the encoder per each revolution of |

-continued

| | |
|---|---|
| | the peristaltic pump 6. |
| Zc – Yc | Number of pulses measured by the encoder (B to D in FIG. 26) during the "n" half-revolutions of the peristaltic pump 6. |
| V2 + V3 + V4 | Volume of air above the low liquid level A. |
| Delta_Encoder_Pulses | Number of pulses measured by the encoder (e.g. 280 pulses) when liquid level is raised from A to B. |
| Pressure_Final | Final pressure after compression (C and D). |
| Pressure_Init | Initial pressure before compression (B). |

The invention claimed is:

1. Method for calibrating a peristaltic pump in a medical apparatus, wherein the medical apparatus comprises a medical machine and a manifold assembly, wherein the medical machine comprises a peristaltic pump and a pressure transducer, and wherein the manifold assembly comprises:

a casing delimiting internally a first compartment and a second compartment;

a yielding pump tube having a first end connected to the first compartment and a second end connected to the second compartment, wherein the yielding pump tube extends outside the casing and is coupled to the peristaltic pump of the medical machine; and a plurality of line tubes each having a first end connected to the first compartment or to the second compartment and a second end connectable to a fluid source or to a drain or to a patient, wherein, when the manifold assembly is properly mounted on the medical machine, an upper part of the second compartment delimits an air buffer volume, the air buffer volume being in communication with the pressure transducer, the method comprising:

i. rotating the peristaltic pump of a predetermined rotation to pump a liquid from the fluid source into the second compartment and raising a level of the liquid in the second compartment to compress air in the air buffer volume;

ii. measuring pressure of air in the air buffer volume;

iii. calculating, from the measured pressure of air in the air buffer volume, a variation of liquid volume in the second compartment due to the rotation of the peristaltic pump; and iv. calculating, from the variation of liquid volume and the predetermined rotation, a stroke liquid volume of the peristaltic pump.

2. The method of claim 1, wherein rotating the peristaltic pump of a predetermined rotation comprises: rotating the peristaltic pump for a plurality of revolutions or fractions of revolutions such that one of a plurality of pressing elements of the peristaltic pump is in a same predetermined position at a start and at an end of the rotation.

3. The method of claim 2, wherein measuring pressure of air in the air buffer volume comprises: measuring an initial pressure before air compression and measuring a final pressure after air compression.

4. The method of claim 3, wherein the level of the liquid is raised starting from a first level and wherein the variation of liquid volume is calculated as a function of an initial air volume above the first level and of the initial pressure and the final pressure; wherein, at the end of the predetermined rotation, the liquid is at a second level.

5. The method of claim 4, wherein the peristaltic pump has two pressing elements; wherein the stroke liquid volume is a ratio between the variation of liquid volume and a number of half-revolutions of the peristaltic pump contained in the predetermined rotation.

6. The method of claim 4, wherein the first level of liquid is obtained by rotating the peristaltic pump until sensing a low liquid level through a low level sensor and further rotating the peristaltic pump of a predetermined angle to pump an extra volume of liquid above the low liquid level in the second compartment; wherein the predetermined position of one of the plurality of pressing elements is the position at the end of the further rotation of the predetermined angle; wherein the first level is the level at the end of the further rotation of the predetermined angle.

7. The method of claim 6, wherein the initial air volume is a difference between a volume of air above the low liquid level and the extra volume of liquid.

8. The method of claim 2 comprising: sensing a high liquid level through a high level sensor and stopping the rotation of the peristaltic pump when one of the plurality of pressing elements is in the predetermined position for a first time after sensing the high liquid level.

9. The method of claim 8, comprising: waiting for a stabilizing time and keeping on measuring pressure after stopping the rotation of the peristaltic pump and before taking a final pressure, to check for possible leakages.

10. The method of claim 1, wherein the medical machine comprises a control unit operatively connected to the peristaltic pump and to the pressure transducer, the peristaltic pump having a plurality of pressing elements and an encoder operatively connected to the control unit to detect position and movement of one of the plurality of pressing elements; wherein the control unit is programmed to rotate the peristaltic pump for a plurality of revolutions or fractions of revolutions such that the pressing element is in a same predetermined position at a start and at an end of the rotation.

11. The method of claim 10, wherein the casing comprises a breathable membrane configured to put into communication the pressure transducer with the air buffer volume; wherein the medical machine further comprises an auxiliary chamber in fluid communication with the air buffer volume, through the breathable membrane, and with the pressure transducer; wherein the method comprises the following step executed by the control unit: measuring an initial pressure before air compression and measuring a final pressure after air compression.

12. The method of claim 11, wherein the medical machine comprises a low level sensor operatively connected to the control unit to sense a low liquid level in the casing, wherein the method comprises the following steps executed by the control unit:

sensing the low liquid level;

further rotating the peristaltic pump of a predetermined angle to pump an extra volume of liquid above the low liquid level in the second compartment;

setting the predetermined position of the pressing element as the position at the end of the further rotation of the predetermined angle, wherein a first level of liquid is reached at the end of the further rotation of the predetermined angle;

rotating the peristaltic pump of the predetermined rotation starting from the predetermined position of the pressing element corresponding to the first level; and calculating the variation of the liquid volume as a function of an initial air volume above the first level and of the initial pressure and the final pressure; wherein the initial air volume is a difference between a volume of air above the low liquid level and the extra volume of liquid.

13. The method of claim 12, wherein the medical machine comprises a high level sensor operatively connected to the control unit and configured to sense a high liquid level in the casing, wherein the method comprises the following step executed by the control unit: stopping the rotation of the peristaltic pump when the pressing element is in the predetermined position for a first time after sensing the high liquid level, wherein, at the end of the predetermined rotation, the liquid is at a second level.

14. The method of claim 13, wherein a first volume delimited in the second compartment below the low level sensor is between 5 ml and 15 ml, wherein a second volume delimited in the second compartment between the low level sensor and the high level sensor is between 15 ml and 25 ml, wherein a third volume delimited in the second compartment above the high level sensor is between 10 ml and 20 ml, and wherein a fourth volume of the auxiliary chamber is between 20 ml and 30 ml.

15. The method of claim 1, wherein calculating the stroke liquid volume through steps i. to iv. is executed consecutively a plurality of times and an average stroke liquid volume is determined.

16. The method of claim 3, wherein the initial pressure is about 0 mmHg and the final pressure is about 400 mmHg.

17. Method for calibrating a peristaltic pump in a medical apparatus, wherein the medical apparatus comprises a medical machine and a manifold assembly, wherein the medical machine comprises a peristaltic pump and a pressure transducer, wherein the manifold assembly comprises:

a casing delimiting internally a first compartment and a second compartment;

a yielding pump tube having a first end connected to the first compartment and a second end connected to the second compartment, wherein the yielding pump tube extends outside the casing and is coupled to the peristaltic pump of the medical machine; and a plurality of line tubes each having a first end connected to the first compartment or to the second compartment and a second end connectable to a fluid source or to a drain or to a patient; wherein, when the manifold assembly is properly mounted on the medical machine, an upper part of the second compartment delimits an air buffer volume, the air buffer volume being in communication with the pressure transducer, the method comprising:

i. rotating the peristaltic pump a predetermined rotation, where the predetermined rotation comprises a plurality of revolutions or fractions of revolutions such that one of a plurality of pressing elements of the peristaltic pump is in a same predetermined position at a start and at an end of the rotation to pump a liquid from the fluid source into the second compartment and raising a level of the liquid in the second compartment to compress air in the air buffer volume;

ii. measuring an initial pressure before air compression and measuring a final pressure after air compression in the air buffer volume;

iii. calculating, from the measured initial pressure and the measured final pressure of air in the air buffer volume, a variation of liquid volume in the second compartment due to the rotation of the peristaltic pump; and iv. calculating, from the variation of liquid volume and the predetermined rotation, a stroke liquid volume of the peristaltic pump, wherein calculating the stroke liquid volume through steps i. to iv. is executed consecutively a plurality of times and an average stroke liquid volume is determined.

18. The method of claim 17, wherein the level of the liquid is raised starting from a first level, wherein the variation of liquid volume is calculated as a function of an initial air volume above the first level and of the initial pressure and the final pressure, and wherein, at the end of the predetermined rotation, the liquid is at a second level.

19. The method of claim 18, wherein the first level of liquid is obtained by rotating the peristaltic pump until sensing a low liquid level through a low level sensor and further rotating the peristaltic pump of a predetermined angle to pump an extra volume of liquid above the low liquid level in the second compartment, wherein the predetermined position of one of the plurality of pressing elements is the position at the end of the further rotation of the predetermined angle, and wherein the first level is the level at the end of the further rotation of the predetermined angle.

20. Medical apparatus comprising a medical machine and a manifold assembly, wherein the medical machine comprises:

a peristaltic pump having a plurality of pressing elements and an encoder to detect a position and movement of one of the plurality of pressing elements;

a pressure transducer; and a control unit operatively connected to the peristaltic pump, the encoder, and to the pressure transducer, the control unit being configured to rotate the peristaltic pump for a plurality of revolutions or fractions of revolutions such that one of the plurality of pressing elements detected by the encoder is in a same predetermined position at a start and at an end of the rotation, wherein the manifold assembly comprises:

a casing delimiting internally a first compartment and a second compartment;

a yielding pump tube having a first end connected to the first compartment and a second end connected to the second compartment, wherein the yielding pump tube extends outside the casing and is coupled to the peristaltic pump of the medical machine; and a plurality of line tubes each having a first end connected to the first compartment or to the second compartment and a second end connected or connectable to a fluid source or to a drain or to a patient; wherein, when the manifold assembly is properly mounted on the medical machine, an upper part of the second compartment delimits an air buffer volume in communication with the pressure transducer, wherein the control unit is configured to calibrate the peristaltic pump by performing the following steps:

rotating the peristaltic pump of a predetermined rotation to pump a liquid from the fluid source into the second compartment and raising a level of the liquid in the second compartment to compress air in the air buffer volume;

measuring pressure of air in the air buffer volume, including measuring an initial pressure before air compression and measuring a final pressure after air compression;

calculating, from the measured pressure of air in the air buffer volume, a variation of liquid volume in the second compartment due to the rotation of the peristaltic pump; and calculating, from the variation of liquid volume and the predetermined rotation, a stroke liquid volume of the peristaltic pump.

21. The apparatus of claim 20, comprising a low level sensor operatively connected to the control unit and configured to sense a low liquid level in the casing, wherein the casing comprises a breathable membrane configured to put into communication the pressure transducer with the air buffer volume, wherein the medical machine further comprises an auxiliary chamber in fluid communication with the air buffer volume, through the breathable membrane, and with the pressure transducer, the control unit being further configured to:

sense the low liquid level;

further rotate the peristaltic pump of a predetermined angle to pump an extra volume of liquid above the low liquid level in the second compartment;

set the predetermined position of the pressing element as the position at the end of the further rotation of the predetermined angle; wherein a first level of liquid is reached at the end of the further rotation of the predetermined angle;

rotate the peristaltic pump of the predetermined rotation starting from the predetermined position of the pressing element corresponding to the first level; and calculate the variation of the liquid volume as a function of an initial air volume above the first level and of the initial pressure and the final pressure, wherein the initial air volume is a difference between a volume of air above the low liquid level and the extra volume of liquid.

* * * * *